(12) United States Patent
Wakamatsu et al.

(10) Patent No.: US 8,646,317 B2
(45) Date of Patent: Feb. 11, 2014

(54) SENSING DEVICE

(75) Inventors: Shunichi Wakamatsu, Sayama (JP); Tomoya Yorita, Sayama (JP); Hiroyuki Kukita, Sayama (JP); Wakako Shinobu, Sayama (JP)

(73) Assignee: Nihon Dempa Kogyo Co., Ltd., Tokyo (JP)

( * ) Notice: Subject to any disclaimer, the term of this patent is extended or adjusted under 35 U.S.C. 154(b) by 918 days.

(21) Appl. No.: 12/802,472

(22) Filed: Jun. 8, 2010

(65) Prior Publication Data
US 2010/0319736 A1    Dec. 23, 2010

(30) Foreign Application Priority Data

Jun. 19, 2009 (JP) ................................. 2009-146985

(51) Int. Cl.
*G01N 29/02* (2006.01)
(52) U.S. Cl.
USPC ........................................................ 73/64.53
(58) Field of Classification Search
USPC .................................. 73/61.49, 61.79, 64.53
See application file for complete search history.

(56) References Cited

U.S. PATENT DOCUMENTS

| 7,036,375 B2* | 5/2006 | Nozaki | 73/579 |
| 2009/0107217 A1* | 4/2009 | Huang | 73/61.42 |
| 2009/0291509 A1* | 11/2009 | Wakamatsu | 436/543 |

FOREIGN PATENT DOCUMENTS

JP    11-183479    7/1999

* cited by examiner

*Primary Examiner* — Daniel S Larkin
(74) *Attorney, Agent, or Firm* — Jordan and Hamburg LLP

(57) ABSTRACT

To provide a sensing device having a high processing power and capable of high-accuracy measurement. It is determined whether or not an oscillation frequency is stabilized while a buffer solution is supplied to a quartz-crystal resonator 4. from a syringe pump 10. When it is determined that the frequency is stabilized, a second valve 14. is switched to a sample solution supply mode to supply a sample solution in an injection loop 14a. to the quartz-crystal resonator 4. An instant at which the sample solution reaches the quartz-crystal resonator 4. and an instant at which the sample solution finishes passing through the quartz-crystal resonator 4. are automatically found based on a supply flow rate of the buffer solution, a volume of the injection loop 14a, a volume of a supply channel supplying the sample solution to the quartz-crystal resonator 4, and an instant at which the second valve 14. is switched to the sample solution supply mode. An oscillation frequency before the sample solution reaches the quartz-crystal resonator 4. and an oscillation frequency after the sample solution passes through the quartz-crystal resonator 4. are found, and a difference between the oscillation frequencies is obtained.

2 Claims, 19 Drawing Sheets

(a)

(b)

(c)

SENSING DEVICE

BACKGROUND OF THE INVENTION

1. Field of the Invention

The present invention relates to a sensing device for recognizing a substance to be sensed contained in a sample solution and determining its quantity based on an oscillation frequency of a piezoelectric resonator such as a quartz-crystal resonator.

2. Description of the Related Art

As a sensing device detecting a trace amount of a substance contained in a sample solution, there has been known a quartz-crystal sensor utilizing a quartz-crystal resonator, and a detection principle of such a quartz-crystal sensor is that an oscillation frequency (resonance frequency) of the quartz-crystal resonator changes when it adsorbs a trace amount of a substance. For example, in such a quartz-crystal sensor, an adsorption layer made of a biological substance film or the like that recognizes a specific substance to be sensed to react therewith is formed on a front surface of a metal electrode (excitation electrode) provided on a quartz-crystal piece. When the adsorption layer is brought into contact with the sample solution, the adsorption layer reacts with the substance to be sensed contained in the sample solution to adsorb the substance to be sensed, resulting in a mass change in the adsorption layer. Since a natural frequency of the quartz-crystal resonator changes according to the mass change of the adsorption layer, the concentration of the substance to be sensed is measured by using this action. As the biological substance film, a film of an antibody reacting with a specific antigen (substance to be sensed) is used, for instance, and this film of the antibody adsorbs the antigen.

A patent document 1 proposes a sensor of a flow-through cell type using a quartz-crystal resonator. In this sensor, the quartz-crystal resonator in which an electrode is formed is provided via silicon rubber between a support substrate and a cover having a solution inflow channel and a solution discharge channel. In the silicon rubber, a hole portion for storing a solution is formed, and a flow-through cell is formed by the cover, the quartz-crystal resonator, and the silicon rubber, and the solution supplied from the inflow channel is discharged from an outflow side after flowing onto the electrode of the quartz-crystal resonator to come into contact with the electrode. Being capable of continuous supply of a liquid, such a sensor of the flow-through cell type has advantages that a frequency characteristic can be easily stabilized, the liquid can be smoothly replaced, and only a small amount of a sample solution is necessary.

In developing a sensing device using a quartz-crystal sensor of such a flow-through cell type, the present inventors have studied the configuration of a system having high processing power and capable of high-accuracy measurement. Though describing the structure of the sensor of the flow-through cell type, the patent document 1 does not describe how the above object is achieved and therefore, the above object cannot be achieved even by the patent document 1.

[Patent document 1] Japanese Patent Application Laid-open No. Hei 11-183479

SUMMARY OF THE INVENTION

The present invention was made under the above circumstances, and has an object to provide a sensing device having a high processing power and capable of high-accuracy measurement.

A sensing device of the present invention is a sensing device in which a piezoelectric sensor including a piezoelectric resonator is mounted and which senses a substance to be sensed in a sample solution based on an oscillation frequency obtained when the sample solution flows from a supply channel to one surface side of the piezoelectric resonator, the sensing device including:

a reference liquid supply part provided to supply a reference liquid to the supply channel and capable of varying a supply flow rate of the reference liquid;

a sample solution storage channel which is interposed between the reference liquid supply part and the supply channel to temporarily store the sample solution, and from which the sample solution is sent to the supply channel by being pushed by the reference liquid supplied from the reference liquid supply part;

a channel switching part switching a channel between a reference liquid supply mode in which the reference liquid supply part is connected to the supply channel not via the sample solution storage channel and a sample solution supply mode in which the reference liquid supply part is connected to the supply channel via the sample solution storage channel;

a control part determining whether or not the oscillation frequency is stabilized while the reference liquid is supplied to the piezoelectric resonator from the reference liquid supply part, and when determining that the oscillation frequency is stabilized, switches the channel switching part to the sample solution supply mode in order to cause the supply of the sample solution in the storage channel to the piezoelectric resonator;

a flow rate setting part via which the supply flow rate of the reference liquid supply part is set; and a computing part which finds an instant at which the sample solution reaches the piezoelectric resonator and an instant at which the sample solution finishes passing through the piezoelectric resonator, based on the supply flow rate of the reference liquid set via the flow rate setting part, a volume of the sample solution storage channel, a volume of the supply channel, and an instant at which the channel switching part is switched to the sample solution supply mode, and finds an oscillation frequency during a period from the switching instant to an instant before the sample solution reaches the piezoelectric resonator and an oscillation frequency after the sample solution passes through the piezoelectric resonator to obtain a difference between the oscillation frequencies.

In this case, the following structure may be adopted.

A liquid feed pump is used as the reference liquid supply part, the sensing device further includes:

a cleaning liquid supply part interposed between the sample solution storage channel and the supply channel to supply a cleaning liquid to the storage channel; and a downstream-side channel switching part provided on a downstream side of the channel switching part to switch a channel between a liquid supply mode in which the storage channel and the supply channel are connected and a cleaning mode in which the storage channel and the cleaning liquid supply part are connected, and for cleaning the storage channel, the channel switching part is switched to the sample solution supply mode, the downstream-side channel switching part is switched to the cleaning mode, and the cleaning liquid is sucked into the storage channel from the cleaning liquid supply part by the reference liquid supply part.

In the present invention, after it is determined that the oscillation frequency is stabilized while the piezoelectric resonator is supplied with the reference liquid, the sample solution is supplied to the piezoelectric resonator by the channel switching part being switched to the sample solution supply mode, which enables the high-accuracy measurement. Further, the occurrence of an extra time not involved in the measurement is reduced and thus a high processing power can be ensured since the instant at which the sample solution reaches the piezoelectric resonator and the instant at which the sample solution finishes passing through the piezoelectric resonator are automatically found, the oscillation frequency before the sample solution reaches the piezoelectric resonator and the oscillation frequency after the sample solution passes through the piezoelectric resonator are found, and the difference therebetween is automatically obtained.

DETAILED DESCRIPTION OF THE PREFERRED EMBODIMENTS

An embodiment of a sensing device according to the present invention will be described by using the drawings.

Figure 1:
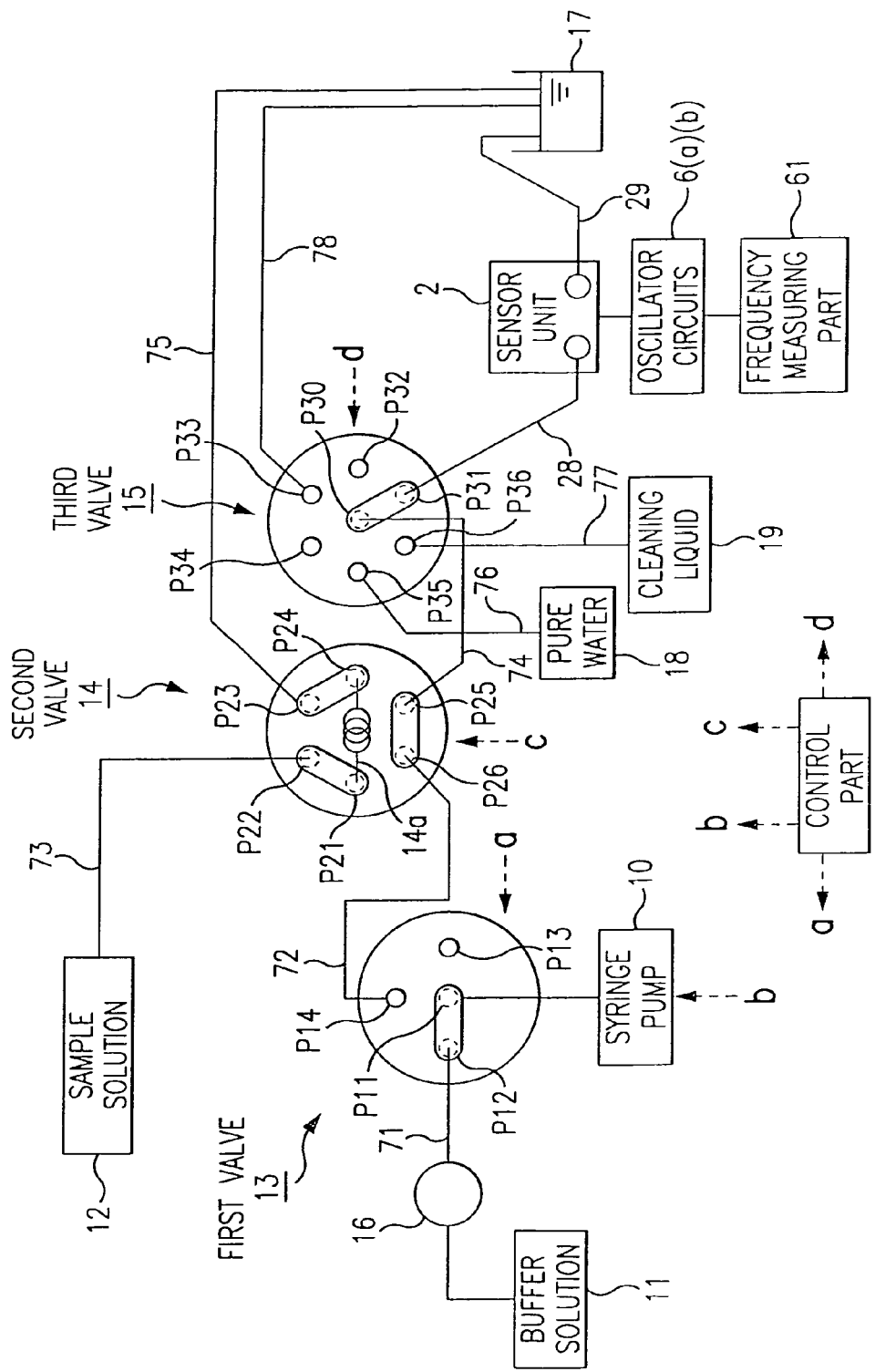
FIG. 1 is a block diagram schematically showing the whole structure of a sensing device according to an embodiment of the present invention.

FIG. 1 is a block diagram showing the whole structure of the sensing device of the present invention, and the sensing device includes a buffer solution reservoir part 11 being a reference liquid reservoir part, a sample solution supply part 12, a first valve 13, a second valve 14, a third valve 15, a sensor unit 2, oscillator circuits 6A, 6B, a frequency measuring part 61, and a control part 100.

The buffer solution reservoir part 11 is a unit storing a buffer solution, for example, a phosphoric acid buffer, and the sample solution supply part 12 is a unit to store, for example, blood or serum being a sample solution and to supply these liquids toward a supply channel provided on a downstream side thereof at a predetermined flow rate. As the sample solution supply part 12, a pipette or a syringe is used, for instance. The supply of the sample solution from the sample solution supply part 12 may be manual, or may be automatic based on a command from the control part 100.

The first valve 13 is provided on a subsequent stage of the buffer solution reservoir part 11 via a degassing part 16. The reason why the degassing part 16 is provided is to prevent the occurrence of a pressure change and a convection change which occurs if dissolved gas in the buffer solution stored in the buffer solution reservoir part 11 vaporizes and bubbles occurs on a sensor or a flow-through cell, thereby preventing the oscillation frequency from becoming unstable. The first valve 13 is composed of the combination of a buffer solution supply part, for example, a syringe pump 10, and a three-way valve. As the buffer solution supply part, a liquid feed pump such as a peristaltic pump can be used, instead of the syringe pump 10.

Figure 2A:
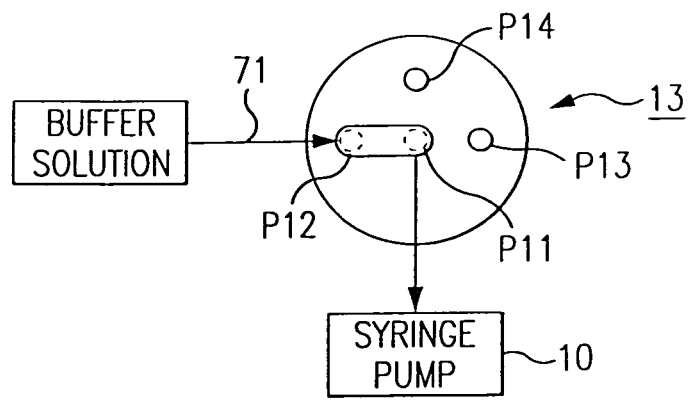
FIG. 2(a) and FIG. 2(b) are explanatory plane views showing switching control of a first valve provided in the sensing device.
Figure 2B:
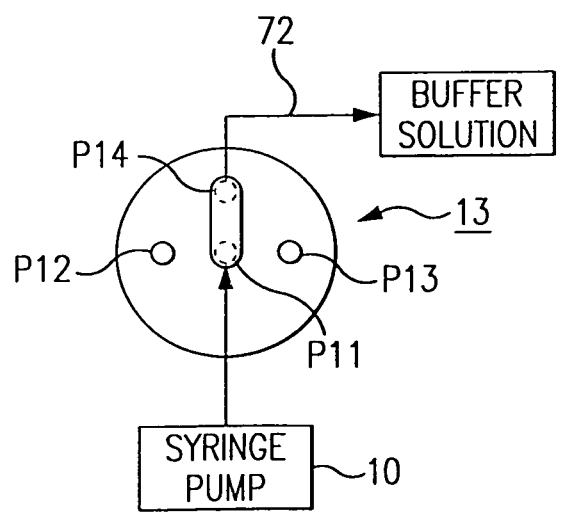

The first valve 13 includes four ports P11 to P14 as shown in FIG. 1, FIG. 2(a), and FIG. 2(b), for instance. Among these ports, the port P12 is connected to the buffer solution reservoir part 11 by a supply channel 71 via the degassing part 16, and the port P14 is connected to the second valve 14 on a subsequent stage by a supply channel 72. The syringe pump 10 sucks and holds the buffer solution stored in the buffer solution reservoir part 11 and supplies the buffer solution at a predetermined supply flow rate. The supply flow rate of the buffer solution is variable and is appropriately set by an operator as will be described later.

The first valve 13 sets the valve to a suction mode in which the port P11 and the port P12 are connected as shown in FIG. 2(a) to suck a predetermined amount of the buffer solution from the buffer solution reservoir part 11 into the syringe pump 10, and sets the valve to a liquid feed mode in which the port P11 and the port P14 are connected as shown in FIG. 2(b) to send the buffer solution in the syringe pump 10 toward the supply channel 72. Further, the first valve 13 is capable of taking air into the syringe pump 10 by connecting the port P11 and the port P13.

Here, in the syringe pump 10, an amount of the buffer solution sucked into the pump 10 is adjusted by the adjustment of a pulling amount of a piston, and a supply flow rate when the buffer solution is sent into the supply channel 72 is controlled by the adjustment of a pressing amount of the piston. The amount of the buffer solution sucked into the pump 10 and the supply flow rate of the buffer solution sent into the supply channel 72 are adjusted by the later-described control part 100 controlling the pulling amount and the pressing amount of the piston based on a set value input by an operator.

Figure 3A:
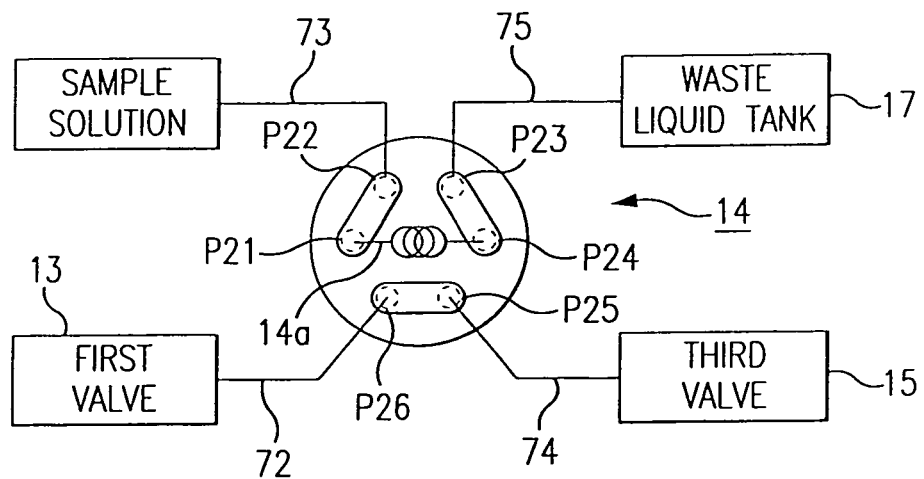
FIG. 3(a) and FIG. 3(b) are explanatory plane views showing switching control of a second valve provided in the sensing device.
Figure 3B:
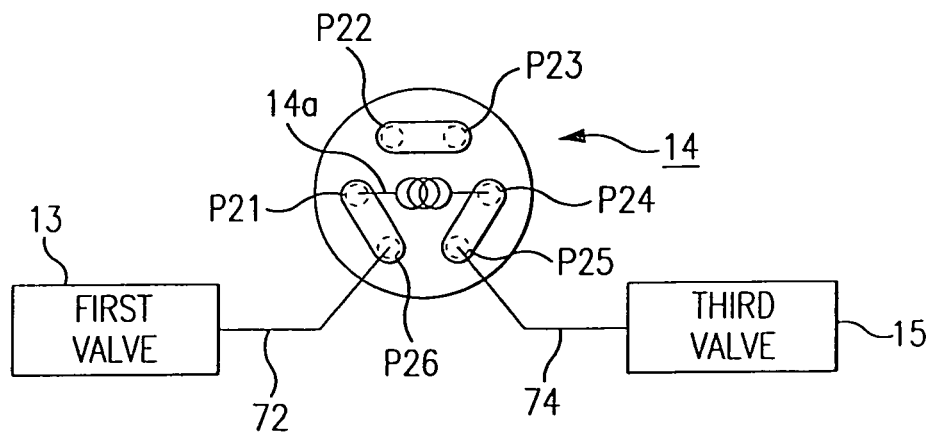

The second valve 14 corresponds to a channel switching part and includes, for example, injection valves. As shown in FIG. 1, FIG. 3(a), and FIG. 3(b), for instance, the second valve 14 includes six ports P21 to P26 and an injection loop 14a serving as a storage channel storing the sample solution.

Among these ports, the port P26 is connected to the supply channel 72 and the port P22 is connected to the sample solution supply part 12 via a supply channel 73. Further, the port P21 is connected to one end side of the injection loop 14a and the port P24 is connected to the other end side of the injection loop 14a. Further, the port P25 is connected to the third valve 15 on a subsequent stage via a supply channel 74 and the port P23 is connected to a waste liquid tank 17 via a discharge channel 75.

As shown in FIG. 3(a), by setting the valves to a buffer solution supply mode in which the port P21 and the port P22, the port P23 and the port P24, and the port P25 and the port P26 are connected, the supply channel 72 extending from the first valve 13 is connected to the supply channel 74 not via the injection loop 14a. In this mode, the buffer solution is sent toward the third valve 15 via the supply channel 74 not via the injection loop 14a. Further, in this mode, the sample solution is led into the injection loop 14a from the sample solution supply part 12, and at this time, when an amount of the led sample solution exceeds a volume of the injection loop 14a, the sample solution is pushed out from the injection loop 14a to be discharged to the waste liquid tank 17 via the discharge channel 75.

Further, as shown in FIG. 3(b), by setting the valves to a sample solution supply mode in which the port P21 and the port P26, the port P22 and the port P23, and the port P24 and the port P25 are connected, the supply channel 72 extending from the first valve 13 is connected to the supply channel 74 via the injection loop 14a. In this mode, the buffer solution is led into the injection loop 14a to push out the sample solution stored beforehand in the injection loop 14a, whereby the sample solution is sent toward the third valve 15 via the supply channel 74.

Figure 4:
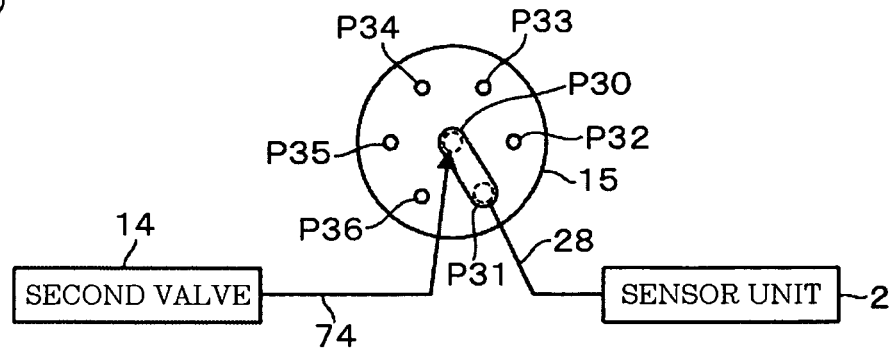
FIG. 4(a) to FIG. 4(c) are explanatory plane views showing switching control of a third valve provided in the sensing device.
Figure 4:
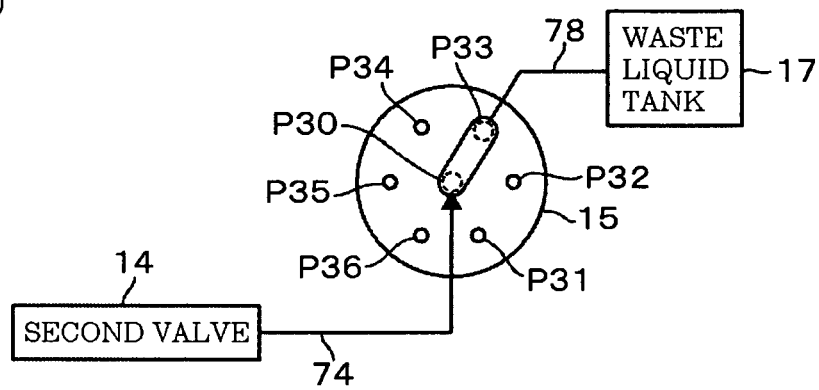
Figure 4:
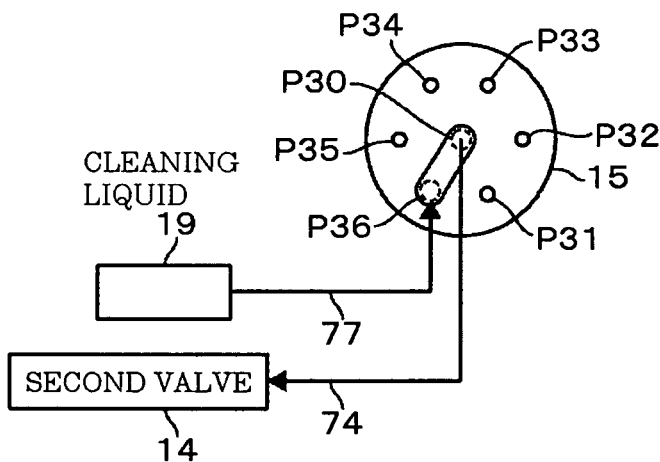

The third valve 15 corresponds to a downstream-side channel switching part, and is constituted by, for example, a six-way valve and includes ports P30 to P36 as shown in FIG. 1, FIG. 4(a), and FIG. 4(b), for instance. Among these ports, the port P30 is connected to the second valve 14 via the supply channel 74, and the port P31 is connected to a liquid supply pipe 28 serving as a supply channel of the present invention supplying a liquid to a sensor unit 2 which will be described later. The port P33 is connected to the waste liquid tank 17 via a discharge channel 78 and the port P35 and the port P36 are connected via a pure water supply channel 76 and a cleaning liquid supply channel 77 to a pure water reservoir part 18 storing pure water and a cleaning liquid reservoir part 19 storing, for example, SDS (Sodium Dodecyl Sulfate) being a cleaning liquid, respectively. In this example, a cleaning liquid supply part is formed by the cleaning liquid supply channel 77 and the cleaning liquid storage part 19. Further, a liquid discharge pipe 29 in the sensor unit 2, which will be described later, is connected to the waste liquid tank 17.

As shown in FIG. 4(a), by setting the valve to a liquid supply mode in which the port P30 and the port P31 are connected, the supply channel 74 extending from the second valve 14 and the liquid supply pipe 28 of the sensor unit 2 are connected and the buffer solution or the sample solution is sent toward the sensor unit 2, and as shown in FIG. 4(b), by setting the valve to a discharge mode in which the port P30 and the port P33 are connected, the sample solution or the like is discharged toward the waste liquid tank 17. Further, by switching the valve to a cleaning mode in which the port P30 and the port P36 are connected, the cleaning liquid supply channel 77 and the supply channel 74 between the third valve 15 and the second valve 14 are connected, and by switching the valve so as to connect the port P30 and the port P35, the pure water supply channel 76 and the supply channel 74 are connected.

Figure 5:
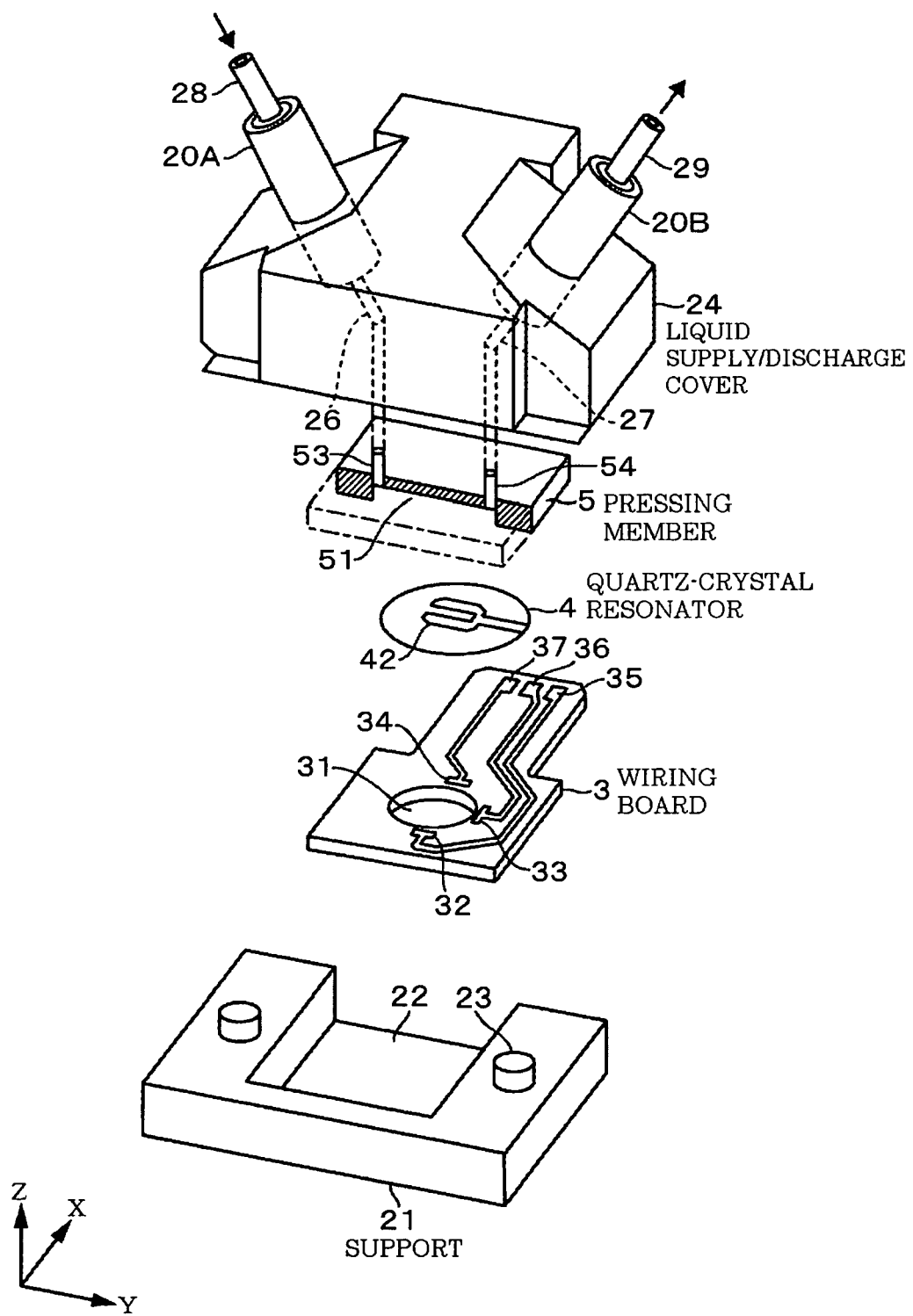
FIG. 5 is an exploded perspective view showing upper surface sides of components of a sensor unit provided in the sensing device.

Next, the sensor unit 2 including a quartz-crystal sensor being a piezoelectric sensor will be described. FIG. 5 is an exploded perspective view showing upper surface sides of components of the sensor unit 2. As shown, the sensor unit 2 is composed of a support 21, a wiring board 3, a quartz-crystal resonator 4, a pressing member 5, and a liquid is supply/discharge cover 24, and these components are stacked in this order from the bottom.

Figure 6A:
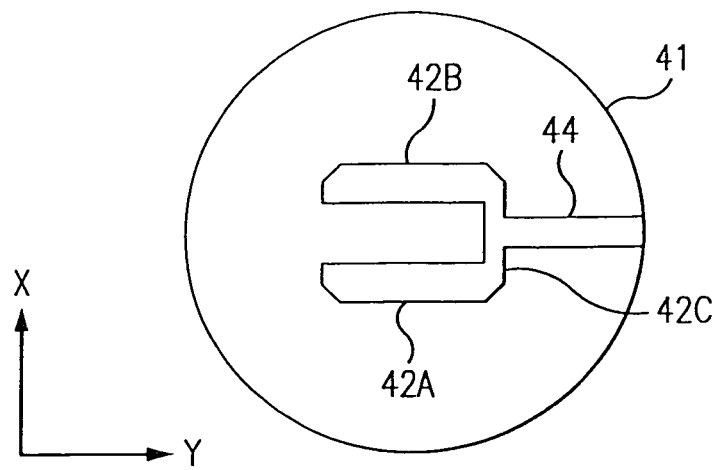
FIG. 6(a) and FIG. 6(b) are a plane view and a bottom view showing excitation electrodes provided on a quartz-crystal piece.
Figure 6B:
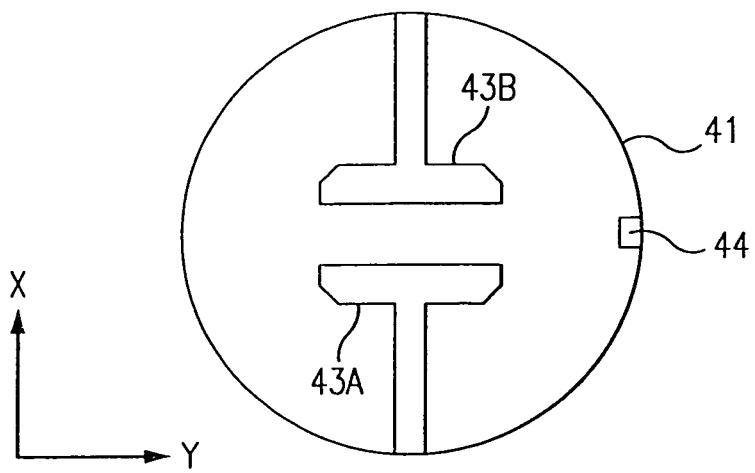

The quartz-crystal sensor has the quartz-crystal resonator 4 being a piezoelectric resonator provided on the wiring board 3. The quartz-crystal resonator 4, as shown FIG. 6(a) and FIG. 6(b), is structured such that excitation electrodes 42, 43 for exciting a quartz-crystal piece 41 in a circular plate shape being a piezoelectric piece are provided on center portions of a front surface and a rear surface of the quartz-crystal piece 41. In this example, the excitation electrode 42 provided on the front surface side includes two excitation electrodes 42A, 42B (a first excitation electrode 42A, a second excitation electrode 42B) in a substantially strip shape extending in a longitudinal direction (Y direction in FIG. 5, FIG. 6(a), and FIG. 6(b)), and these excitation electrodes 42A, 42B are provided in parallel with each other, being apart from each other in a width direction (X direction in FIG. 5, FIG. 6(a), and FIG. 6(b)). Further, an electrode film 42C is connected to a longitudinal one end of each of the excitation electrodes 42A, 42B. A lead electrode 44 is connected to the electrode film 42C, and the lead electrode 44 is formed so as to be drawn out toward a peripheral edge on one-end side of the quartz-crystal piece 41 and bent along an end surface of the quartz-crystal piece 41 to be led to the rear surface side. The excitation electrodes 42A, 42B, the electrode film 42, and the lead electrode 44 are integrally formed.

Figure 7:
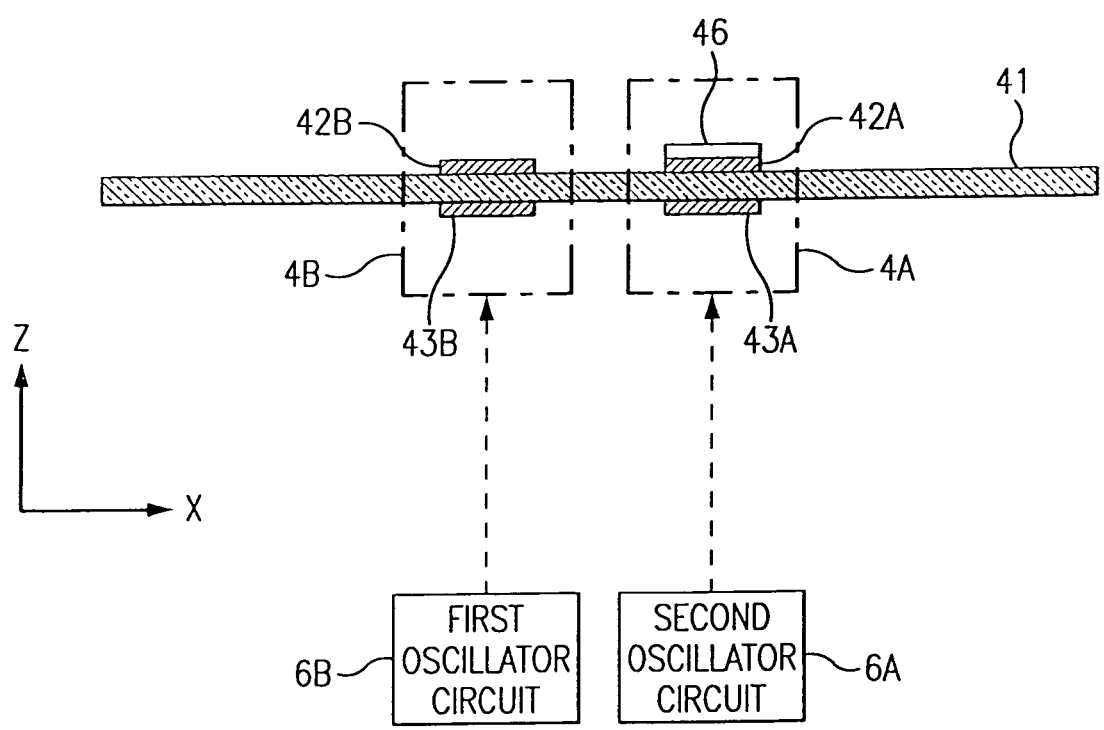
FIG. 7 is a vertical sectional view showing a first oscillation area and a second oscillation area provided on the quartz-crystal piece.

The excitation electrode 43 provided on the rear surface side is formed in the same layout as the two excitation electrodes 42A, 42B so as to face the two excitation electrodes 42A, 42B on the front surface side across the quartz-crystal piece 41. In this example, as shown in FIG. 7, on the common quartz-crystal piece 41, a first oscillation area 4A is constituted by an area where the excitation electrodes 42A, 43A are formed and a second oscillation area 4B is constituted by an area where the excitation electrodes 42B, 43B are formed.

The excitation electrodes in one of the two oscillation areas 4A, 4B, for example, the excitation electrodes 42A, 43A in the first oscillation area 4A are used as reaction electrodes for detecting a substance to be sensed, and the excitation electrodes 42B, 43B in the other second oscillation area 4B, for example, are used as reference electrodes. For this purpose, as shown in FIG. 7, an adsorption layer 46 containing an adsorption substance that adsorbs the substance to be sensed is formed on the excitation electrode 42A on the front surface side (side in contact with the sample solution) in the first oscillation area 4A. With this structure, the substance to be sensed is not adsorbed by the excitation electrode 42B in the second oscillation area 4B. Therefore, by comparing the oscillation frequencies of the areas 4A, 4B before and after the adsorption of the substance to be sensed, it is possible to cancel a frequency change caused by the viscosity of the sample solution and by the adhesion of a substance other than the substance to be sensed and to sense a change (decrease amount) of the oscillation frequency corresponding to an amount of the substance to be sensed adsorbed by the adsorption layer 46.

The wiring board 3 is constituted by, for example, a printed circuit board, and in the wiring board 3, formed is a through hole 31 serving as a concave portion forming an airtight space faced by the excitation electrodes 43A, 43B on the rear surface side of the quartz-crystal resonator 4, and the through hole 31 is formed to have a diameter large enough to house the excitation electrodes 43A, 43B. Further, on a front surface of the wiring board 3, an electrode 32, an electrode 33, and an electrode 34 are provided around the through hole 31 at spaced intervals. The electrodes 32, 33, 34 are formed so as to be electrically connected to the excitation electrode 43A on the rear surface side, the lead electrode 44 led to the rear surface side from the front surface side, and the excitation electrode 43B on the rear surface side respectively when the quartz-crystal resonator 4 is disposed on the wiring board 3. On a back end side of the wiring board 3, there are provided connection terminals 35, 36, 37, which are electrically connected to the electrodes 32, 33, 34 via conductive paths respectively. Among them, the connection terminal 36 is connected to the ground.

Figure 8:
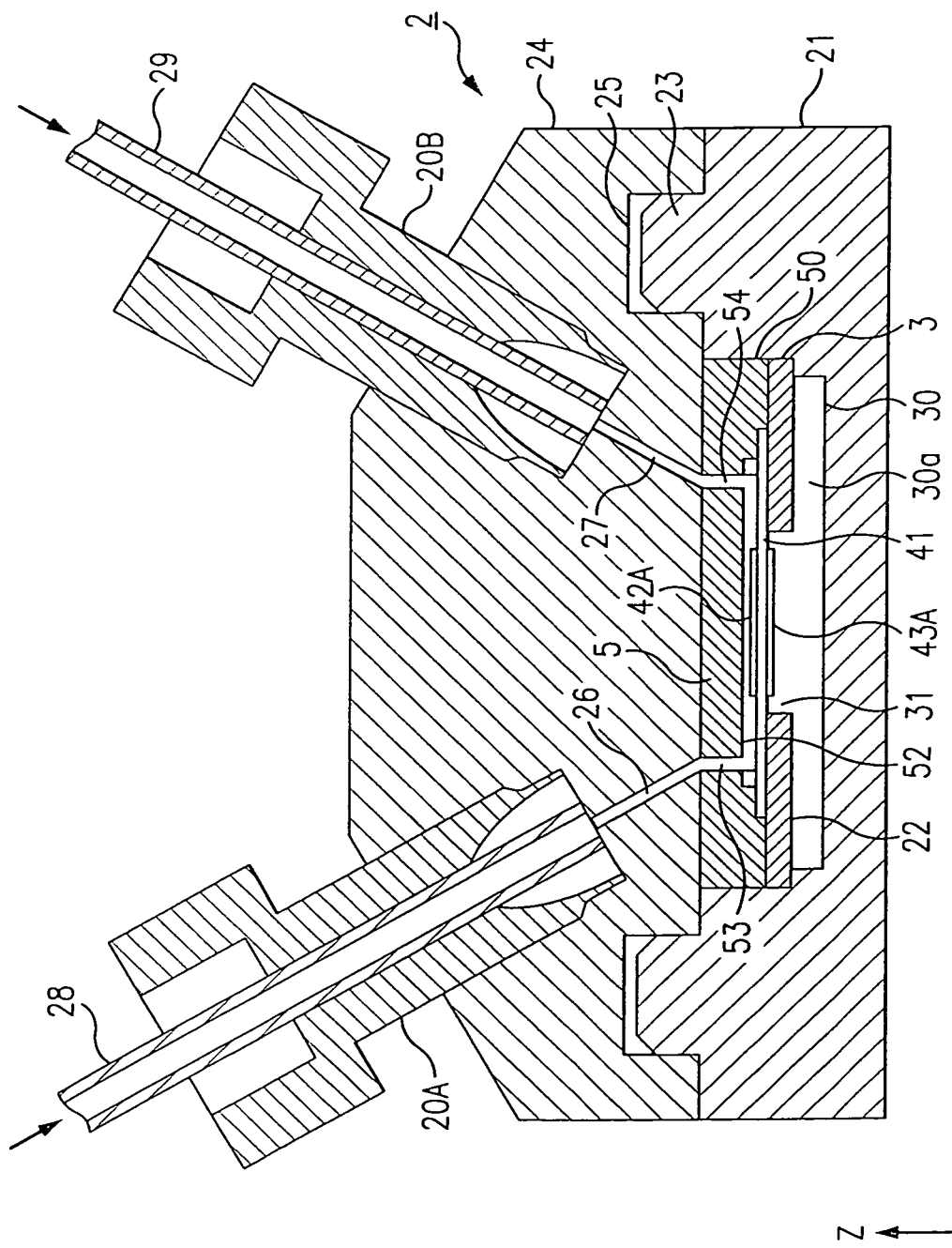
FIG. 8 is a view showing a vertical section of the sensor unit.
Figure 9:
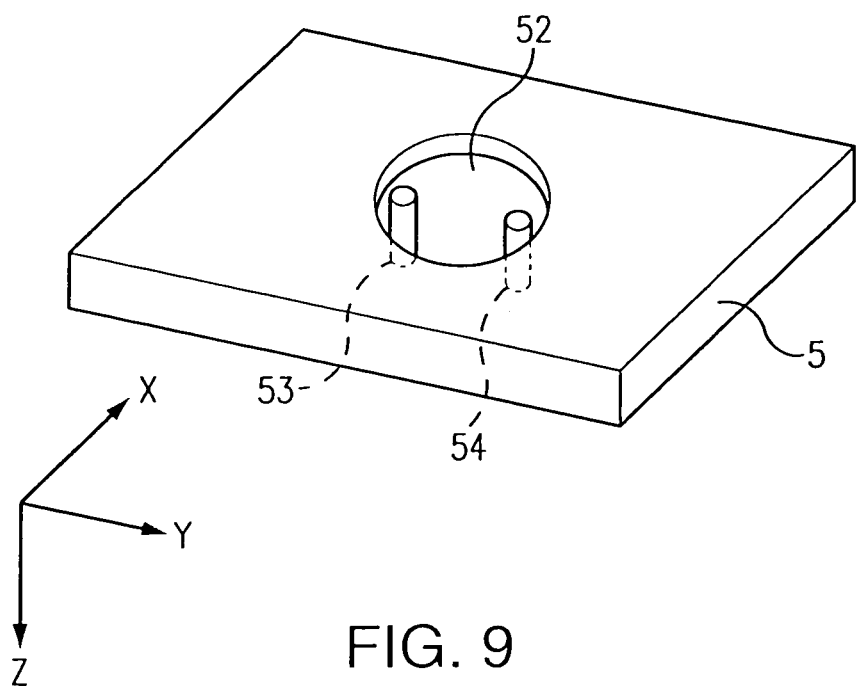
FIG. 9 is a perspective view showing a pressing member seen from a bottom surface side.

The pressing member 5 is formed in a shape corresponding to a shape of the wiring board 3 by using an elastic member, for example, silicon rubber, and as shown in FIG. 8, a lower surface of a rim area 50 of the pressing member 5 is in contact with an area, of the wiring board 3, outside the quartz-crystal resonator 4. The pressing member 5 plays a role of not only pressing the quartz-crystal resonator 4 against the wiring board 3 but also demarcating and forming a liquid storage space 51 on the excitation electrodes 42A, 42B. For this purpose, as shown in a bottom view of the pressing member 5 in FIG. 9, a concave portion 52 in, for example, a circular shape is formed in a bottom surface of the pressing member 5 to surround the excitation electrodes 42A, 42B. Further, in an upper surface of the pressing member 5, a supply channel 53 for supplying a liquid to the liquid storage space 51 and a discharge channel 54 for discharging a liquid from the liquid storage space 51 are formed.

In the support 21, a concave portion 22 having a shape corresponding to the shape of the wiring board 3 is formed, and projections 23 are formed on parts of its upper surface. The wiring board 3 is housed in the concave portion 22. On a lower surface of the supply/discharge cover 24, concave portions 25 are formed, and the supply/discharge cover 24 is positioned to the support 21 when the projections 23 provided on the support 21 are fit in the concave portions 25.

Further, as shown in FIG. 5 and FIG. 8, in the liquid supply/discharge cover 24, a liquid supply channel 26 communicating with the supply channel 53 is provided, and a liquid discharge channel 27 communicating with the discharge channel 54 is provided. The liquid supply pipe 28 and the liquid discharge pipe 29 are connected to the liquid supply channel 26 and the liquid discharge channel 27 respectively. In the drawings, 20A denotes a supply port, and 20B denotes a discharge port.

Figure 10:
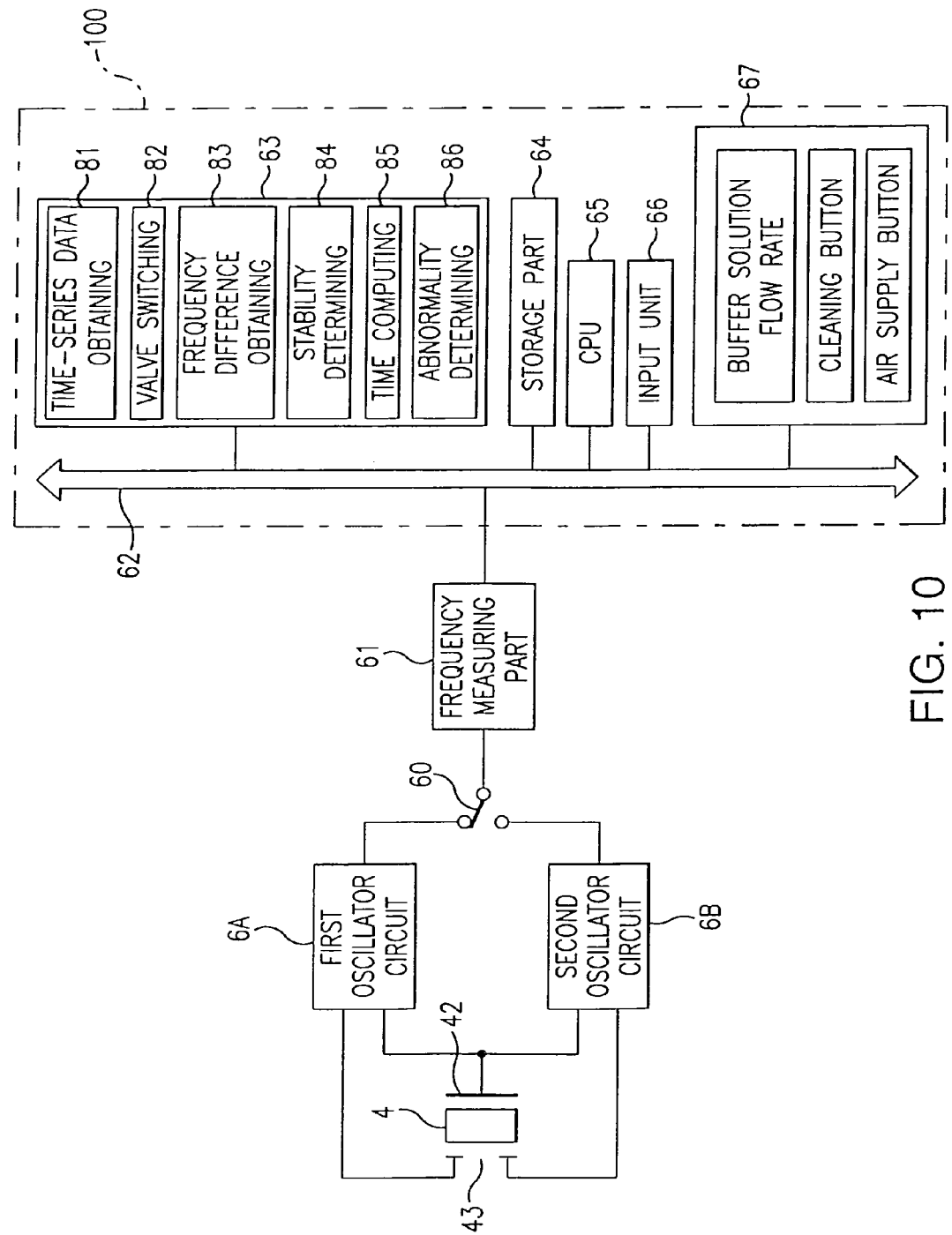
FIG. 10 is a block diagram showing an example of a frequency measuring part and a control part provided in the sensing device.

In the foregoing, the quartz-crystal resonator 4 and the wiring board 3 correspond to the piezoelectric sensor of the present invention. The rear surface side of the quartz-crystal resonator 4 is exposed to an airtight atmosphere. Therefore, this piezoelectric sensor constitutes a Languban-type quartz-crystal sensor. As shown in FIG. 10, the first and second oscillation areas 4A, 4B described above are electrically connected to the first oscillator circuit 6A and the second oscillator circuit 6B of a Colpitts type, which are connected in series to the first and second oscillation areas 4A, 4B respectively via signal lines connected to the connection terminals 35, 37 formed on the wiring board 3, so that oscillation frequencies are extracted from the first oscillation area 4A and the second oscillation area 4B. A frequency measuring part 61 is connected to the first oscillator circuit 6A and the second oscillator circuit 6B via a switch part 60, and oscillation outputs (frequency signals) from the first and second oscillator circuits 6A, 6B are alternately taken into the frequency measuring part 61 via the switch part 60. The frequency measuring part 61 may be one that detects the frequencies by a frequency counter, which is a publicly known circuit, but may be one that uses a method of A/D-converting the frequency signals, processing the resultants by a carrier move, generating rotation vectors rotating at the frequencies of the frequency signals, and finding the velocities of the rotation vectors, as described in, for example, Japanese Patent Application Laid-open No. 2006-258787. The use of the measuring part that performs such digital processing enables frequency detection with higher accuracy and therefore is more preferable.

The frequency signals thus obtained are sampled every 1 sec., for instance, by a program stored in a program storage part 63 in the control part 100 and the sampled frequency signals are stored as time-series data in a storage part 64. Here, in FIG. 10, 62 denotes a bus, and the control part 100 and the bus 62 are each constituted by a computer. The control part 100 includes the program storage part 63, the storage part 64, a CPU 65, an input unit 66, a display part 67, and so on.

In the program storage part 63, in addition to a program 81 including a step group for sampling the time-series data, there are stored a program 82 including a step group for performing switching sequence of the valves, a program 83 including a step group for finding the frequency decreases (frequency differences) when the sample solution is supplied to the sensor unit 2, based on the time-series data, a program 84 including a step group for determining whether the frequency is stabilized while the buffer solution is supplied to the sensor unit 2, a program 85 including a step group for calculating the instant at which the sample solution reaches the quartz-crystal resonator 4 and the instant at which the sample solution finishes passing through the quartz-crystal resonator 4, a program 86 including a step group for determining whether any of the oscillation frequencies from the sensor unit 2 has abnormality or not, and so on.

First, the frequency stability determining program 84 will be described. In the step group thereof, whether or not the oscillation frequency of the quartz-crystal resonator 4 is stabilized is calculated based on an Allan Deviation expression shown in the following expression (1), for instance.

$$\sigma_y^2(\tau) = \sigma_y^2(\tau, m) = \frac{1}{m}\sum_{k=1}^{m}\frac{1}{2}(y_{k+1} - y_k)^2 \qquad (1)$$

Figure 11:
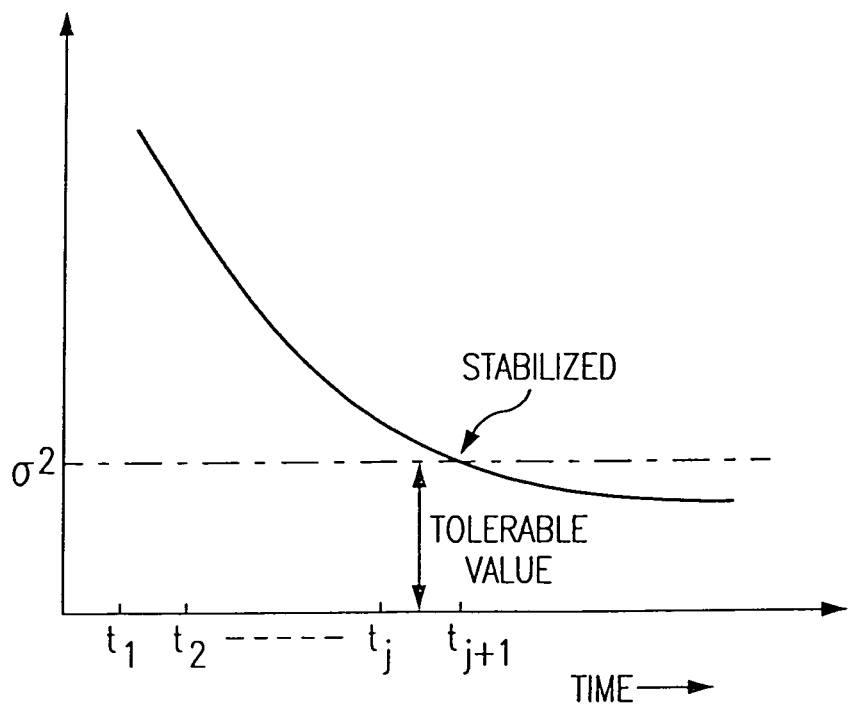
FIG. 11 is an explanatory characteristic chart showing a method of determining frequency stabilization.

In the expression (1), $y_k$ is a frequency obtained at the time of the k-sampling in each sampling span and m is the number of samples included in each sampling span (k, m: positive number). In this example, a difference in the oscillation frequency ($y_{k+1}-y_k$) is calculated, for example, one second after the sampling is started upon the supply of the buffer solution to the sensor unit 2, and values each equal to a squared value of the difference in the frequency oscillation are added until a measurement time passes (until m pieces of the frequencies are obtained), and a measurement result $\sigma^2$ that is the addition result divided by 2m is calculated. The measurement time is calculated by the later-described time computing program 85. Then, since the above measurement result $\sigma^2$ decreases to a certain value as the oscillation frequency stabilizes with the elapse of time from the start of the sampling as shown in FIG. 11, the aforesaid program 84 determines that the frequency has stabilized when the measurement result $\sigma^2$ becomes smaller than a preset frequency tolerable value and outputs a sample solution supply enable signal to the second valve 14. For example, the above determination on the frequency stability is performed for the oscillation frequency of the first oscillation area 4A or for both of the oscillation frequencies of the first oscillation area 4A and the second oscillation area 4B.

Next, the time computing program 85 will be described. The instant at which the sample solution reaches the quartz-crystal resonator 4 refers to an instant at which the sample solution reaches the liquid storage space 51, and is calculated based on an instant at which the second valve 14 is switched to the sample solution supply mode, a volume of a first channel extending from a downstream end of the injection loop 14a up to an upstream end of the liquid storage space 51, and the supply flow rate of the buffer solution.

Specifically, the sample solution is sent toward the sensor unit 2 from the instant at which the second valve 14 is switched to the sample solution supply mode, and since at this time, the sample solution flows from the injection loop 14a by being pushed out by the buffer solution, the supply flow rate of the buffer solution corresponds to a supply flow rate of the sample solution. The first supply channel extending from the downstream end of the injection loop 14a up to the upstream end of the liquid storage space 51 is composed of the supply channel 74 connected to the downstream end of the injection loop 14a, the third valve 15, the liquid supply pipe 28, the liquid supply channel 26, and the supply channel 53. Since the volume of the first channel is known in advance, with the knowledge of the supply flow rate of the sample solution passing therethrough, it is possible to calculate the time from the instant at which the second valve 14 is switched to the sample solution supply mode up to an instant T1 at which the sample solution reaches the liquid storage space 51, that is, up to a reaction start instant at which the reaction starts between the adsorption layer 46 and the substance to be sensed. Concretely, when the volume of the whole first channel is 60 µliters and the supply flow rate of the sample solution is 60 µliters/minute, the reaction start instant T1 is 60 seconds after the second valve 14 is switched to the sample solution supply mode.

Further, the instant at which the sample solution finishes passing through the quartz-crystal resonator 4 refers to an instant at which all the sample solution in the injection loop 14a finishes passing through the liquid storage space 51, and is calculated based on the instant at which the second valve 14 is switched to the sample solution supply mode, a volume of the injection loop 14a, a volume of a second channel from the downstream end of the injection loop 14a up to a downstream end of the liquid storage space 51, and the supply flow rate of the buffer solution. In this case, since the injection loop 14a is filled with the sample solution, the volume of the injection loop 14a corresponds to a volume of the sample solution.

The second channel is the combination of the first channel and the liquid storage space 51. Dividing the sum of the volume of the second channel and the volume of the sample solution by the flow rate of the sample solution gives the time from the instant at which the second valve 14 is switched to the sample solution supply mode up to an instant T2 at which all the sample solution stored in the injection loop 14a is discharged from the liquid storage space 51, that is, up to a reaction end time. Concretely, if the volume of the whole second channel is 66 µliters, the volume of the sample solution is 120 µliters, and the supply flow rate of the sample solution is 60 µliters/minute, the reaction end time T2 is 180 seconds after the second valve 14 is switched to the sample solution supply mode.

Figure 12:
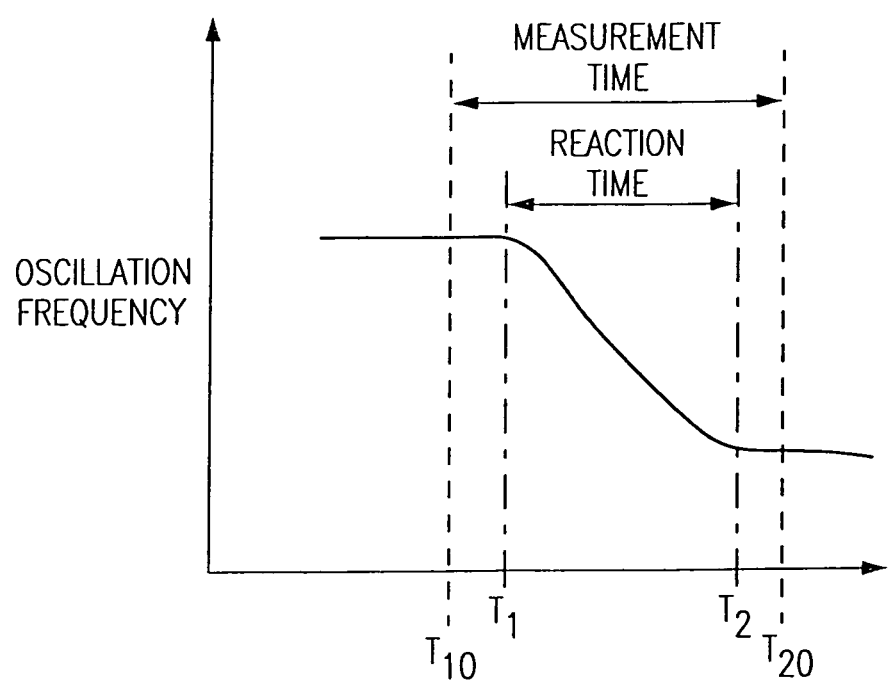
FIG. 12 is an explanatory characteristic chart showing measurement time and reaction time.

Then, as shown in FIG. 12, based on the calculation results, an instant T10 before the sample solution reaches the liquid storage space 51, for example, 30 seconds before the arrival instant T1, and an instant T20 after the sample solution passes through the liquid storage space 51, for example, 30 seconds after the passage end instant T2 are found, and a signal to the effect that the oscillation frequencies at these instants T10, T20 should be obtained and differences between these oscillation frequencies should be obtained is output to the frequency difference obtaining program 83.

The instant before the sample solution reaches the liquid storage space 51 is set to about 10 seconds to about 30 seconds before the arrival instant T1, for instance, and the instant after the sample solution passes through the liquid storage space 51 is set to about 10 seconds to about 30 seconds after the passage end instant T2, for instance.

Based on the signal, the frequency obtaining program 83 obtains an oscillation frequency A0 of the first oscillator circuit 6A at the instant T10 and an oscillation frequency of the second oscillator circuit 6B at the instant T10, obtains an oscillation frequency A1 of the first oscillator circuit 6A at the instant. T20 and an oscillation frequency B1 of the second oscillator circuit 6B at the instant T20, and calculates {(A1−A0)−(B1−B0)} which is difference data of the above oscillation frequencies.

In this embodiment, the programs 85 and 83 correspond to a computing part.

Further, in the time computing program 85, the aforesaid measurement time is also calculated, and this measurement time refers to the time from the instant T10 at which the oscillation frequencies are obtained before the sample solution reaches the liquid storage space 51 up to the instant T20 at which the oscillation frequencies are obtained after the sample solution passes through the liquid storage space 51, and the reaction time refers to the time during which the supply of the sample solution to the quartz-crystal resonator 4 is continued and is the time from the instant T1 at which the sample solution reaches the liquid storage space 51 up to the instant T2 at which the sample solution finishes passing through the liquid storage space 51, as shown in FIG. 12.

Further, the abnormality determining program 86 is provided with a function of monitoring the oscillation frequencies after the quartz-crystal resonator 4 is oscillated in the sensor unit 2 and determining whether or not there is abnormality in any of the oscillation frequencies. Since the oscillation frequencies are sampled every 1 sec., an abrupt change of any of the sampled oscillation frequencies leads to the determination that the abnormality has occurred. The abrupt change mentioned here refers to a change in the oscillation frequency by ±0.1% or more. As previously described, the oscillation frequencies greatly change at instants at which the supply of the buffer solution and the sample solution to the quartz-crystal resonator 4 is started. A rough variation in the oscillation frequencies in such cases is known in advance, and therefore, in the determination on the abnormality, the variation in the oscillation frequencies at these timings is taken into consideration. Then, when it is determined that any of the oscillation frequencies is abnormal, an alarm output signal is output on the display part 67 and alarm is displayed on the display part 67, and a driving stop signal for the syringe pump 10 is output to cause the stop of the supply of the buffer solution and the sample solution to the quartz-crystal resonator 4, and the like. At this time, the third valve 15 may be switched to the position of P33.

The input unit 66 also serves as a flow rate setting part for the setting of the supply flow rate of the buffer solution, and the supply flow rate of the buffer solution can be set via the input unit 66, and when a cleaning button and an air supply button displayed on the display part 67 is set to ON via the input unit 66, it is also possible to execute a cleaning process and an air supply process. Further, on the display part 67, a measurement end, ends of the cleaning process and the air supply process, and the like are also displayed, for instance.

In this embodiment, a control part which determines whether or not the oscillation frequency is stabilized while the buffer solution is supplied to the quartz-crystal resonator 4, and when determining that the oscillation frequency is stabilized, switches the second valve 14 to the sample solution supply mode to cause the supply of the sample solution in the storage channel to the quartz-crystal resonator 4 is composed of the frequency stabilization determining program 84 and the valve switching program 82. A computing part which finds the instant at which the sample solution reaches the quartz-crystal resonator 4 and the instant at which the sample solution finishes passing through the quartz-crystal resonator 4 and finds the oscillation frequency before the sample solution reaches the quartz-crystal resonator 4 and the oscillation frequency after the sample solution passes through the quartz-crystal resonator 4 to obtain the difference between these oscillation frequencies is composed of the frequency difference obtaining program 83 and the time computing program 85.

Figure 13:
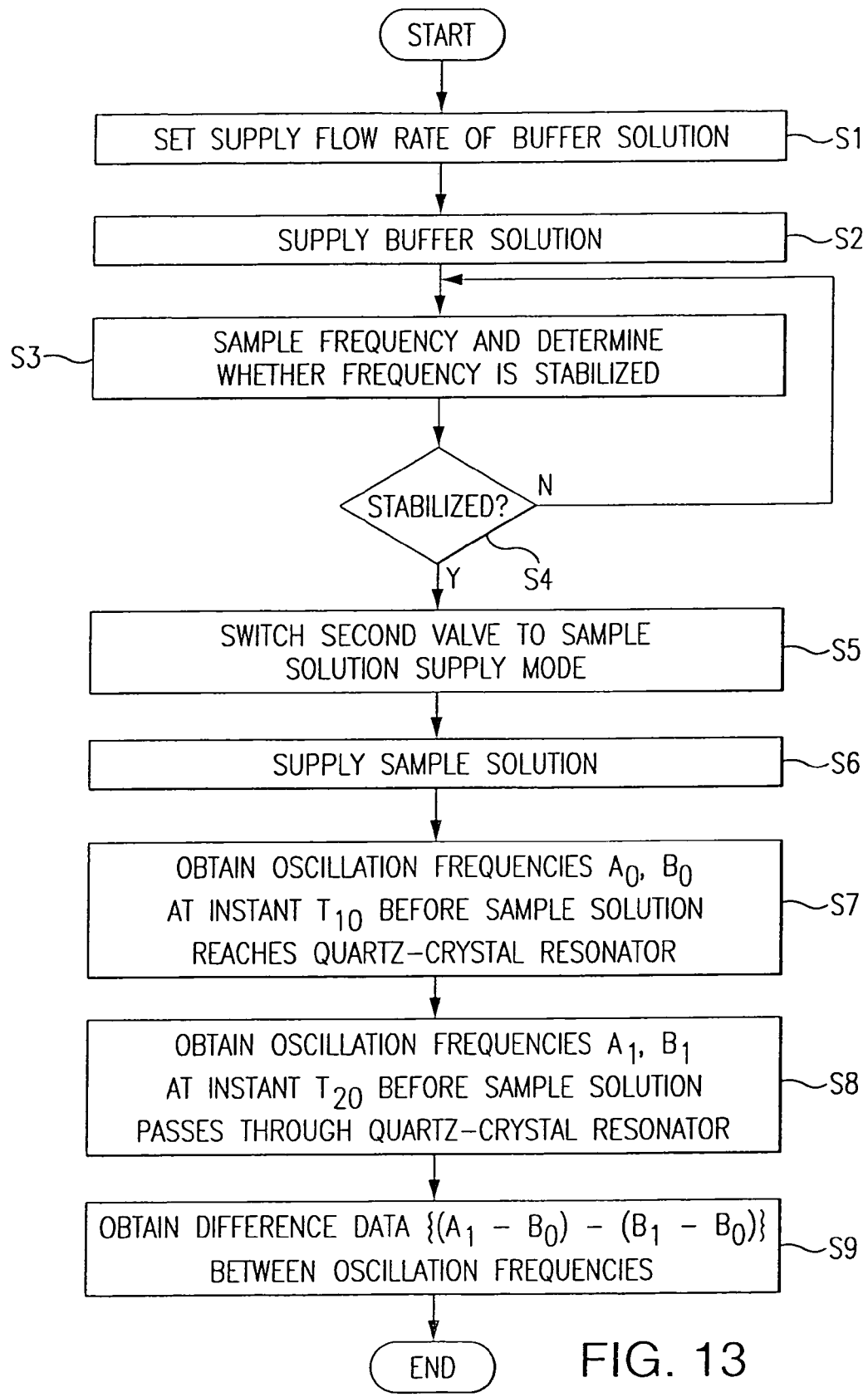
FIG. 13 is an explanatory flowchart showing the operation of the sensing device.
Figure 14A:
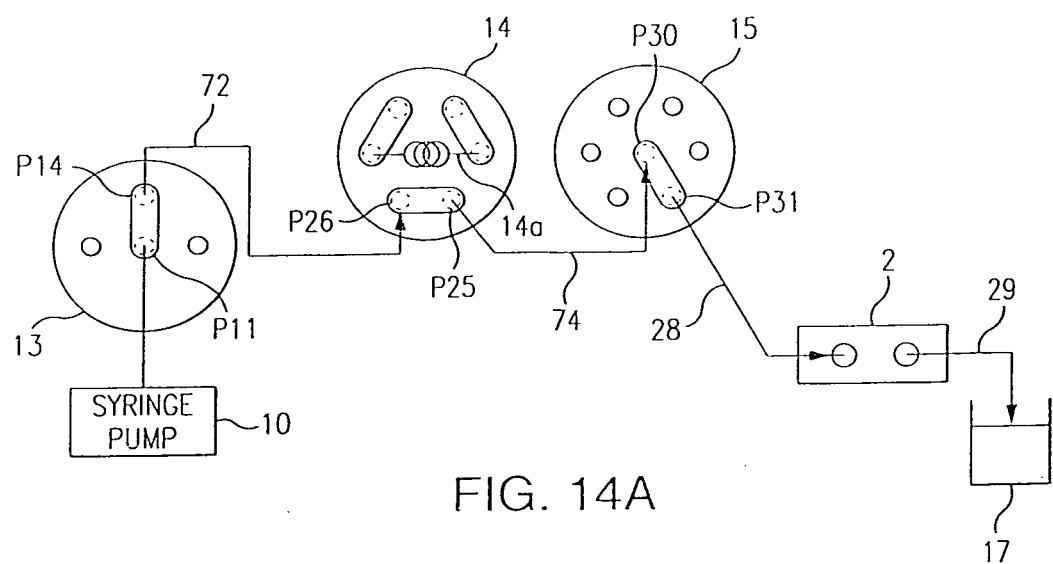
FIG. 14(a) and FIG. 14(b) are views showing the operation of the sensing device.
Figure 14B:
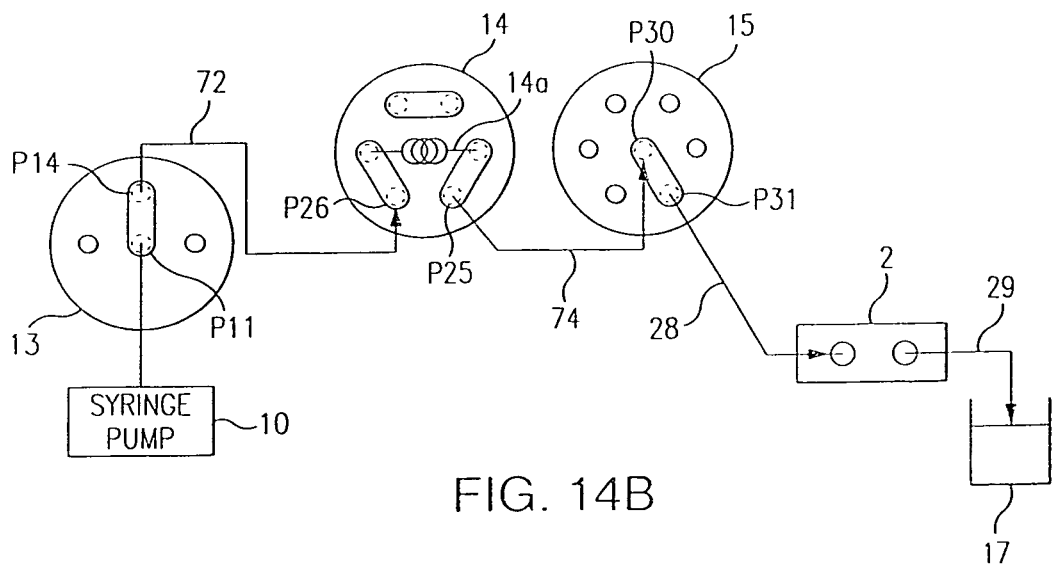

Next, the operation of the sensing device will be described with reference to FIG. 13, FIG. 14(*a*), and FIG. 14(*b*). First, the quartz-crystal resonator 4 is mounted in the sensor unit 2 to be airtightly integrated with the sensor unit 2, and the oscillation areas 4A, 4B and the oscillator circuits 6A, 6B are electrically connected respectively via the connection terminals 35 to 37 formed on the wiring board 3. Then, for example, an operator sets the supply flow rate of the buffer solution according to the sample solution as a target of the measurement (Step S1), and supplies the sample solution so as to fill the injection loop 14*a*.

Next, the oscillation of the quartz-crystal resonator 4 (oscillation areas 4A, 4B) is started with a predetermined frequency, for example, 30 MHz by the oscillator circuits 6A, 6B respectively, and at the same time, the buffer solution in the buffer solution reservoir part 11 is sucked into the syringe pump 10. Then, for example, by setting the first valve 13 to the third valve 15 to the positions shown in FIG. 14(*a*) (at this time, the second valve 14 is set to the buffer solution supply mode), the supply channel 72 extending from the first valve 13 is connected to the supply channel 74 on the downstream side of the second valve 14 not via the injection loop 14*a*, so that the buffer solution is supplied into the liquid storage space 51 of the sensor unit 2 via the third valve 15 and the liquid supply pipe 28 (Step S2). Incidentally, the buffer solution is temporarily sucked into the syringe pump 10 by the syringe pump 10 and is sent from here at the set supply flow rate.

The oscillation frequencies of the oscillation areas 4A, 4B are sampled in the frequency measuring part 61 and decrease to certain values when the buffer solution is supplied. The oscillation frequency of the quartz-crystal resonator 4 at this time changes since the oscillation state is unstable immediately after it starts to oscillate, and thereafter stabilizes with the elapse of time. Then, as previously described, it is determined whether or not the oscillation frequency is stabilized (Step S3), and when it is determined that the oscillation frequency is stabilized (Step S4), the second valve 14 is switched to the sample solution supply mode as shown in FIG. 14(*b*) (Step S5).

Consequently, the supply channel 72 extending from the first valve 13 is connected to the supply channel 74 on the downstream side of the second valve 14 via the injection loop 14*a*. In this manner, the buffer solution is supplied into the injection loop 14*a*, and the sample solution in the injection loop 14*a* is pushed out by the buffer solution to be supplied into the liquid storage space 51 (Step S6). Then, the oscillation frequencies A0, B0 at the instant T10 before the sample solution reaches the quartz-crystal resonator 4 are obtained (Step S7), then, the oscillation frequencies A1, B1 at the instant T20 after the sample solution passes through the quartz-crystal resonator 4 are obtained (Step S8), and the difference data $\{(A1-A0)-(B1-B0)\}$ between these oscillation frequencies is obtained (Step S9).

Here, when the sample solution is supplied into the liquid storage space 51 and the substance to be sensed comes into contact with the adsorption layer 46 of the excitation electrode 42A, the substance to be sensed is adsorbed by the adsorption layer 46 due to, for example, an antigen-antibody reaction, a chemical reaction, or the like, and the oscillation frequency of the quartz-crystal resonator 4 (oscillation area 4A) decreases due to a mass load effect. Then, when the liquid storage space 51 is kept supplied with the sample solution all during the reaction time, the substance to be sensed in an amount according to the concentration of the substance to be sensed in the sample solution is adsorbed by the adsorption layer 46, so that the oscillation frequency of the quartz-crystal resonator 4 (excitation electrode 42A) decreases to a certain value. Therefore, at the instant T20, since all the sample solution has been supplied, the substance to be sensed is adsorbed by the adsorption layer 46 according to the concentration of the substance to be sensed in the sample solution.

The difference data thus obtained is a frequency difference after a variation in the frequency due to the viscosity of the sample solution, the adhesion of a substance other than the substance to be sensed, and the like is cancelled, and is a frequency difference ascribable only to the adsorption of the substance to be sensed. For example, this value is used for creating a calibration curve showing a correspondence relation between the concentration of the substance to be sensed in the sample solution and a decrease amount in the frequency, or for detecting the concentration or the presence/absence of the substance to be sensed in the sample solution with reference to the calibration curve created beforehand.

After the difference data is thus obtained, "measurement end" is displayed on the display part 67, for instance. Thereafter, for executing the air supply process, the operator sets the "air supply button" to ON in the input unit 66, and for executing the cleaning process, sets the "cleaning button" to ON in the input unit 66.

Next, the air supply process will be described. When the "air supply button" is set to ON, for example, the first to third valves 13 to 15 are switched so that the channel system is set to the state shown in FIG. 14(*b*), all the buffer solution remaining in the syringe pump 10 is sent, and the buffer solution is discharged to the waste liquid tank 17 via the liquid storage space 51. Next, by switching the first valve 13 so as to connect the port P11 and the port P13, a predetermined amount of air is taken into the syringe pump 10. Then, by setting the channel system to the state shown in FIG. 14(*b*), the air is supplied to the channel system by the syringe pump 10. Consequently, a liquid component remaining in the channel including the liquid storage space 51 is pushed out by the air. After the air is thus supplied into the channel by the syringe pump 10 for a preset time, "air supply process end" is displayed on the display part 67, for instance. In this air supply process, an amount of the air taken into the syringe pump 10, a supply flow rate and supply time of the air supplied to the channel system, and so on are set in advance, for instance. By the air supply process thus executed, since the liquid component remaining in the channel is blown away by the supplied air, the sample solution and the buffer solution remaining in the liquid storage space 51 are efficiently removed, which makes it possible to constantly keep the sensor unit 2 in a sanitarily good state.

Figure 15A:
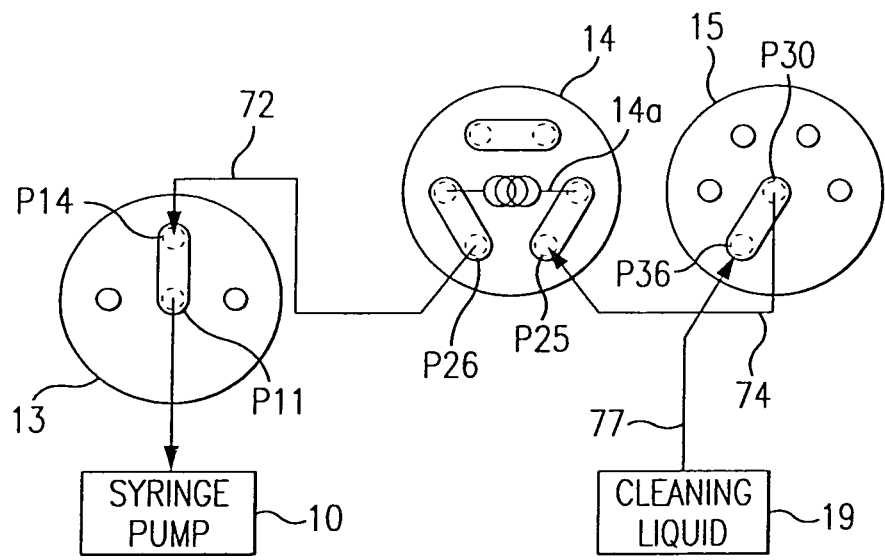
FIG. 15(a) and FIG. 15(b) are views showing the operation of the sensing device.
Figure 15B:
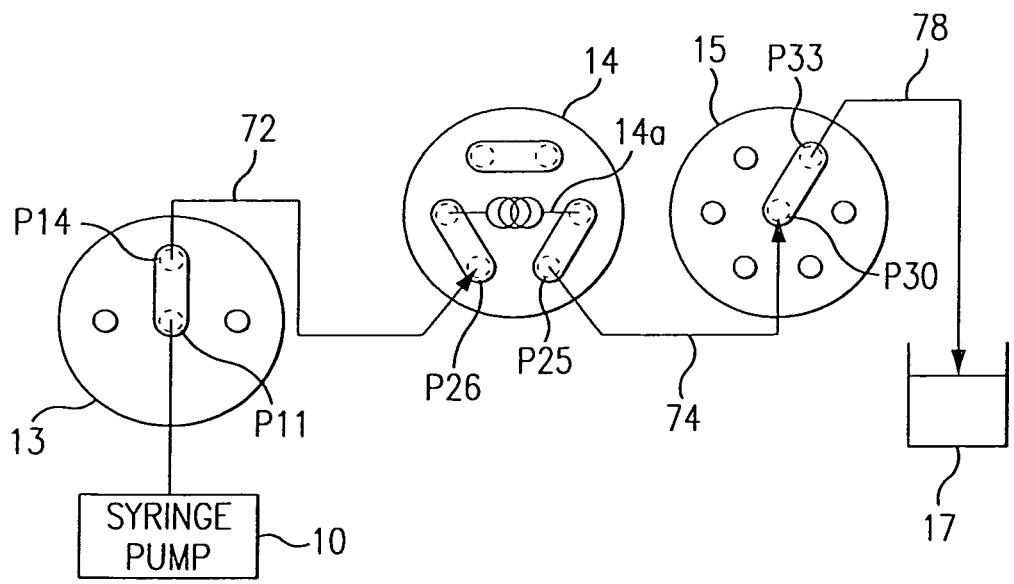

Next, the cleaning process will be described. When the "cleaning button" is set to ON, the first to third valves 13 to 15 are switched so that the channel system is set to the state shown in FIG. 15(*a*) (the third valve 15 is set to the cleaning mode), so that the injection loop 14*a* and the cleaning liquid supply channel 77 are connected via the supply channel 74 and the injection loop 14*a* and the syringe pump 10 are connected via the supply channel 72. Then, after the cleaning liquid in the cleaning liquid supply part 19 is sucked by the syringe pump 10 to, for example, an upstream end of the injection loop 14*a*, the third valve 15 is switched to the discharge mode as shown in FIG. 15(*b*), so that the cleaning liquid in the injection loop 14*a* is discharged to the waste liquid tank 17 by the syringe pump 10. In this cleaning process, since the cleaning liquid flows in the injection loop 14*a*, an extraneous matter in the injection loop 14*a* is washed away by the cleaning liquid to be removed.

The cleaning process is followed by a rinsing process, for instance. In the rinsing process, for example, the third valve 15 is switched so as to connect the supply channel 74 and the pure water supply channel 76, and the other channel system is set to the state shown in FIG. 15(*a*), so that pure water is sucked by the syringe pump 10 to the upstream end of the injection loop 14*a*. Next, by switching the third valve 15 as shown in FIG. 15(*b*), the pure water in the injection loop 14*a* is discharged by the syringe pump 10 to the waste liquid tank 17 via the channels. Consequently, the cleaning liquid remaining in the injection loop 14*a* is washed away by the pure water. In the cleaning process and the rinsing process, amounts of the cleaning liquid and the pure water sucked into the syringe pump 10, supply flow rates of the cleaning liquid and pure water sent to the channel system, and so on, for example, are set in advance.

Here, the air supply process is performed at the end of the measurement, for instance, and the cleaning process is performed at the time of the maintenance which is performed once a day, but at a predetermined timing after the measurement in the quartz-crystal resonator 4 is finished, one of or both of these air supply process and cleaning process may be performed automatically. Here, when the both are performed, the air supply process preferably comes before the cleaning process.

In the above-described embodiment, when the first oscillation area 4A and the second oscillation area 4B are formed on the common quartz-crystal piece 41 and the first excitation electrode 42A is used as the reaction electrode and the second excitation electrode 42B is used as the reference electrode, variations in the frequencies due to the viscosity of the sample solution and the adhesion of a substance other than the substance to be sensed in the sample solution are equal both for the oscillation frequencies A1, B1 of the oscillation areas 4A, 4B when the both areas are brought into contact with the sample solution, and therefore, by taking a difference between the oscillation frequencies of the oscillation areas 4A, 4B, it is possible to cancel a frequency variation due to these reasons. Therefore, when the difference between the oscillation frequencies A1, A0 of the oscillation area 4A when the oscillation area 4A is brought into contact with the sample solution and the buffer solution (A1−A0) is compared with the difference between the oscillation frequencies B0, B1 when the oscillation area 4B is brought into contact with the sample solution and the buffer solution (B1−B0), the obtained variation {(A1−A0)−(B1−B0)} between these differences can be regarded as a frequency variation ascribable to an amount of the substance to be sensed in the sample solution. Consequently, it is possible to obtain a highly reliable variation in the oscillation frequency.

Further, it is determined whether or not the frequency is stabilized after the buffer solution is supplied to the sensor unit 2, and when the frequency is stabilized, the sample solution is supplied to the sensor unit 2 by switching the second valve 14, which enables the measurement with high processing power and with high accuracy. Specifically, if an operator manually switches the valve and drives the syringe pump, the timings for switching the valves and driving the pump differ depending on each operator, and therefore, the high-accuracy measurement cannot be sometimes executed because the sample solution is supplied to the sensor unit 2 before the frequency is stabilized after the supply of the buffer solution, or the measurement time is sometimes uselessly becomes long because the buffer solution is kept supplied to the sensor unit 2 even after the frequency is stabilized after the supply of the buffer solution. On the other hand, according to the above-described structure, since the liquid supplied to the sensor unit 2 is automatically changed from the buffer solution to the sample solution immediately when the oscillation frequency is stabilized after the supply of the buffer solution to the sensor unit 2, the obtained data on the oscillation frequencies is highly accurate, and the useless supply of the buffer solution is prevented and thus it is possible to prevent the measurement time from becoming long, which can ensure high processing power.

Further, since the cleaning liquid is sucked by the syringe pump 10 to be led into the injection loop 14*a* and then the cleaning liquid is discharged by the syringe pump 10 toward the waste liquid tank 17, the inside of the injection loop 14*a* can be cleaned easily and in a short time. Using the syringe pump 10 at this time makes it possible to adjust a flow rate of the cleaning liquid sucked into the injection loop 14*a* and a flow rate of the cleaning liquid discharged from the injection loop 14*a*, and when an adhesion amount of some kind of the sample solution to the injection loop 14*a* is large, it is possible to easily perform the control of, for example, increasing the flow rate to increase a cleaning power.

In the cleaning process, the channel supplying the buffer solution may be cleaned in such a manner that the cleaning liquid is led to a position short of the syringe pump 10 or the second valve 14 is set to the buffer solution supply mode to lead the cleaning liquid into the channel. By sufficiently removing an extraneous matter remaining in the channel in this manner, it is possible to prevent the adhesion of a substance other than the substance to be sensed in the sample solution to the quartz-crystal resonator 4, which enables the high-accuracy measurement of the oscillation frequencies.

Furthermore, in the abnormality determining program 85, it is determined whether or not the oscillation frequencies of the oscillator circuits 6A, 6B have abnormality and when the abnormality occurs, the alarm is displayed and the driving of the syringe pump 10 is stopped to stop the supply of the sample solution and the buffer solution. Therefore, a trouble such as liquid leakage or the abnormality of the quartz-crystal sensor can be immediately detected, which enables the quick execution of a solution work. Therefore, even if some trouble occurs, it is possible to minimize the time during which the measurement cannot be performed due to the trouble.

Figure 16:
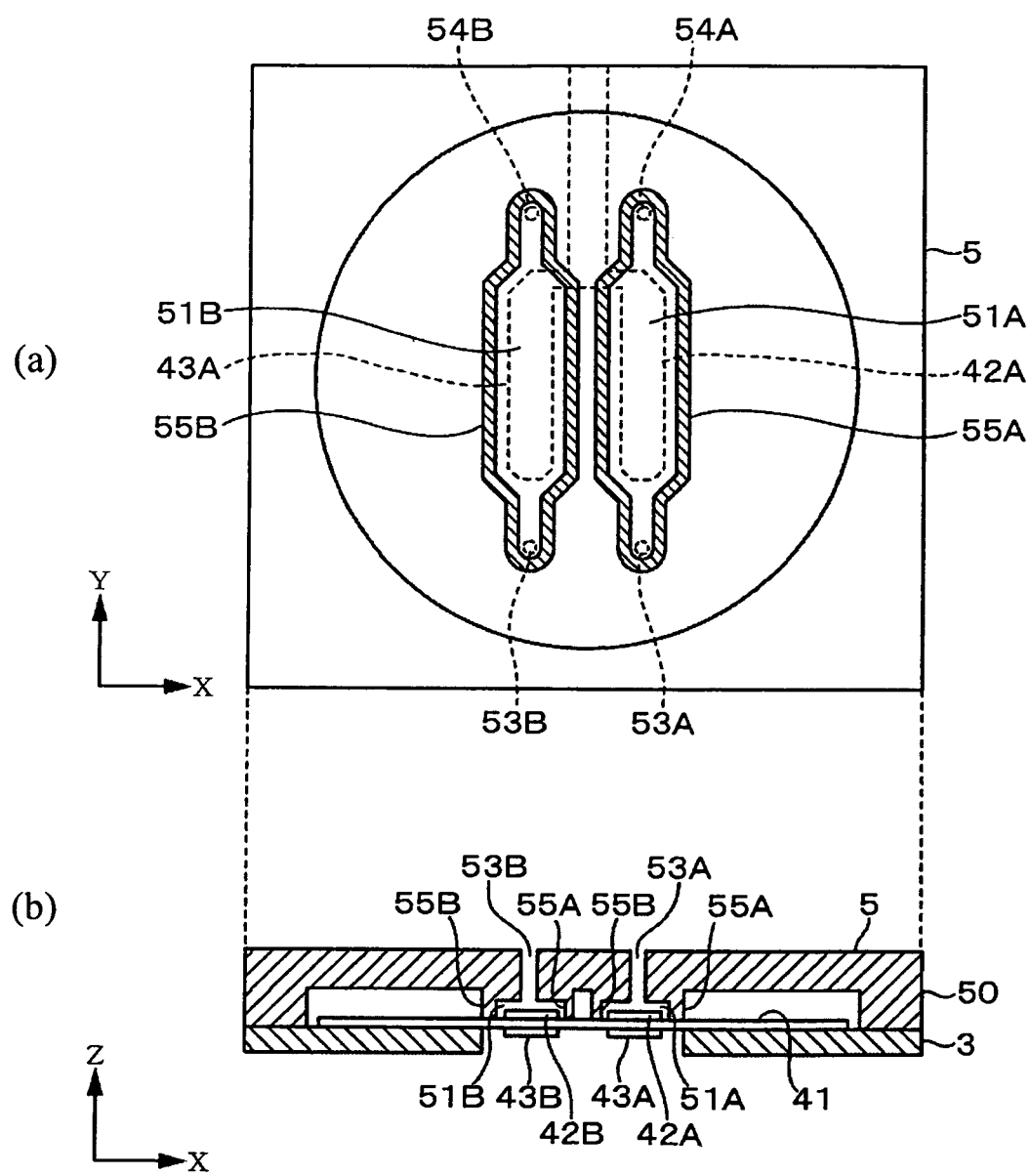
FIG. 16(a) and FIG. 16(b) are a bottom view showing a pressing member and a vertical sectional view showing part of a sensor unit respectively, in another example.

In the foregoing, the present invention is also applicable to a quartz-crystal sensor in which separate liquid storage spaces 51A, 51B are formed on the first excitation electrode 4A and the second excitation electrode 4B respectively. In this case, the pressing member 5 includes, on its bottom surface, a first annular projection 55A and a second annular projection 55B surrounding peripheries of the two excitation electrodes 42A, 42B respectively as shown in a bottom view in FIG. 16(*a*) and a vertical sectional view in FIG. 16(*b*) of the pressing member 5, and by the pressing member 5 being pressed toward the front surface of the quartz-crystal resonator 4, the first liquid storage space 51A and the second liquid storage space 51B are formed on the front surfaces of the first excitation electrode 42A and the second excitation electrode 43B respectively.

Figure 17:
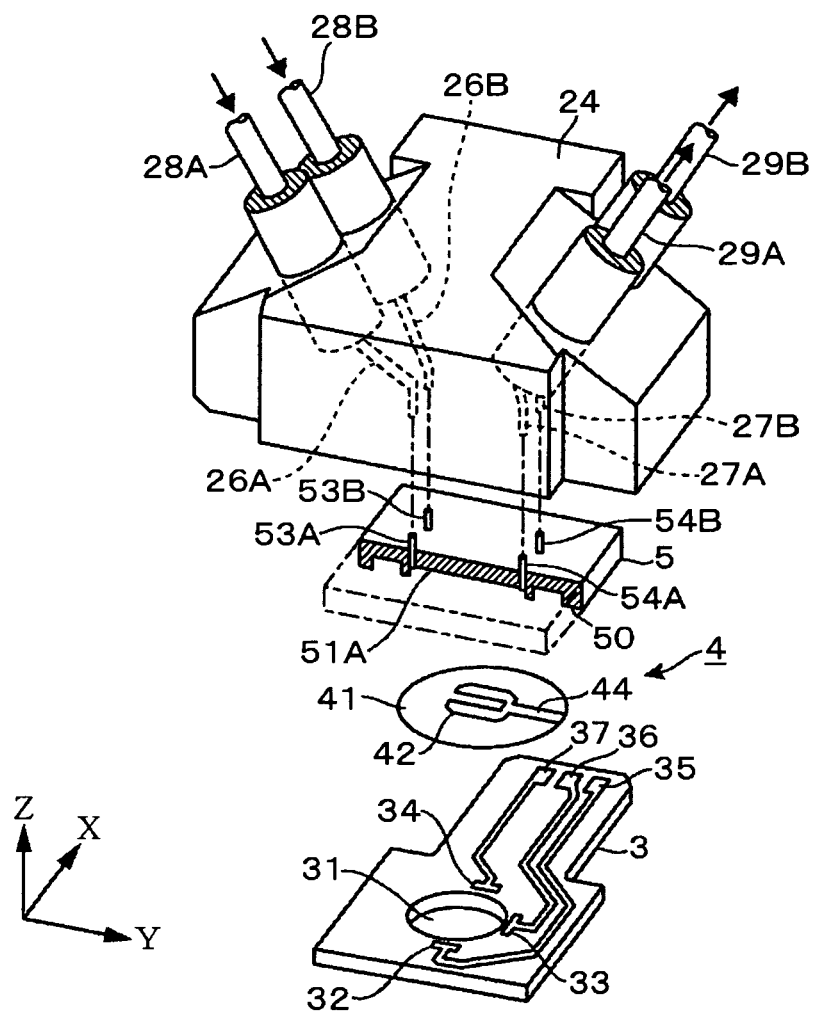
FIG. 17 is an exploded perspective view showing the sensor unit in the other example.
Figure 17:
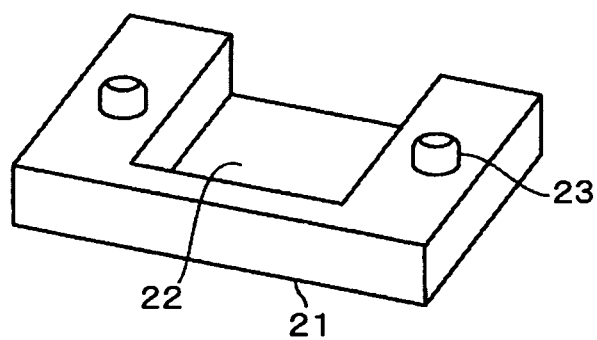
Figure 18:
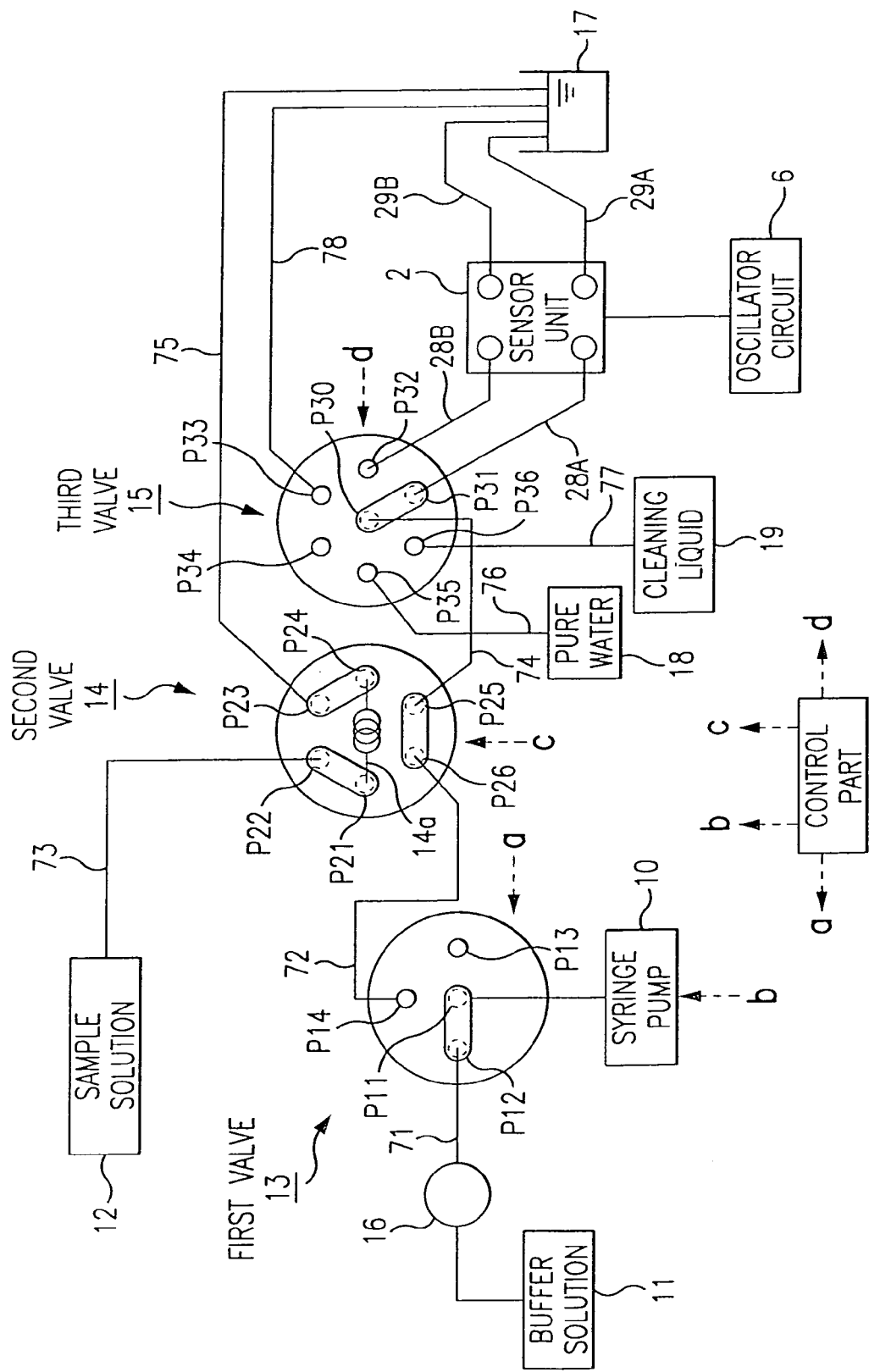
FIG. 18 is a block diagram schematically showing the whole structure of a sensing device in the other example.

The first liquid storage space 51A and the second liquid storage space 51B are supplied with a liquid via a first supply channel 53A and a second supply channel 53B respectively, and the liquid thus supplied is discharged via a first discharge channel 54A and a second discharge channel 54B respectively. As shown in FIG. 17, a first liquid supply pipe 28A and a second liquid supply pipe 28B are connected to the liquid supply/discharge cover 24 and communicate with the first supply channel 53A and the second supply channel 53B via liquid supply channels 26A, 26B respectively. Further, a first liquid discharge pipe 29A and a second liquid discharge pipe 29B are connected to the liquid supply/discharge cover 24 and communicate with a first discharge channel 54A and a second discharge channel 54B via a liquid discharge channel 27A and a liquid discharge channel 27B respectively. As shown in FIG. 18, the port P31 of the third valve 15 is connected to the first liquid supply pipe 28A and the port P32 is connected to the second liquid supply pipe 28B.

In this case, since a half amount of the sample solution stored in the injection loop 14a is sent to each of the first liquid storage space 51A and the second liquid storage space 51B, the time computing program 85 calculates, as the instant at which the sample solution reaches the quartz-crystal resonator 4, both an instant T3 at which the sample solution reaches the first liquid storage space 51A and an instant T4 at which the sample solution reaches the second liquid storage space 51B, and as the instant at which the sample solution finishes passing through the quartz-crystal resonator 4, calculates both an instant T5 at which the sample solution finishes passing through the first liquid storage space 51A and an instant T6 at which the sample solution finishes passing through the liquid storage space 51B. Then, for example, 10 seconds before the instant T3 and the instant T4 at which the sample solution reaches the first and second liquid storage spaces 51A, 51B are defined as an instant T30 and an instant T40 before the sample solution reaches the first and second liquid storage spaces 51A, 51B, and for example, 10 seconds after the instants T5, T6 at which the sample solution finishes passing through the first and second liquid storage spaces 51A, 51B are defined as instants T51, T61 after the sample solution passes through the first and second liquid storage spaces 51A, 51B. The volume of the sample solution supplied to each of the first and second liquid storage spaces 51A, 51B used for this calculation is a half of the volume of the injection loop 14a.

Figure 19:
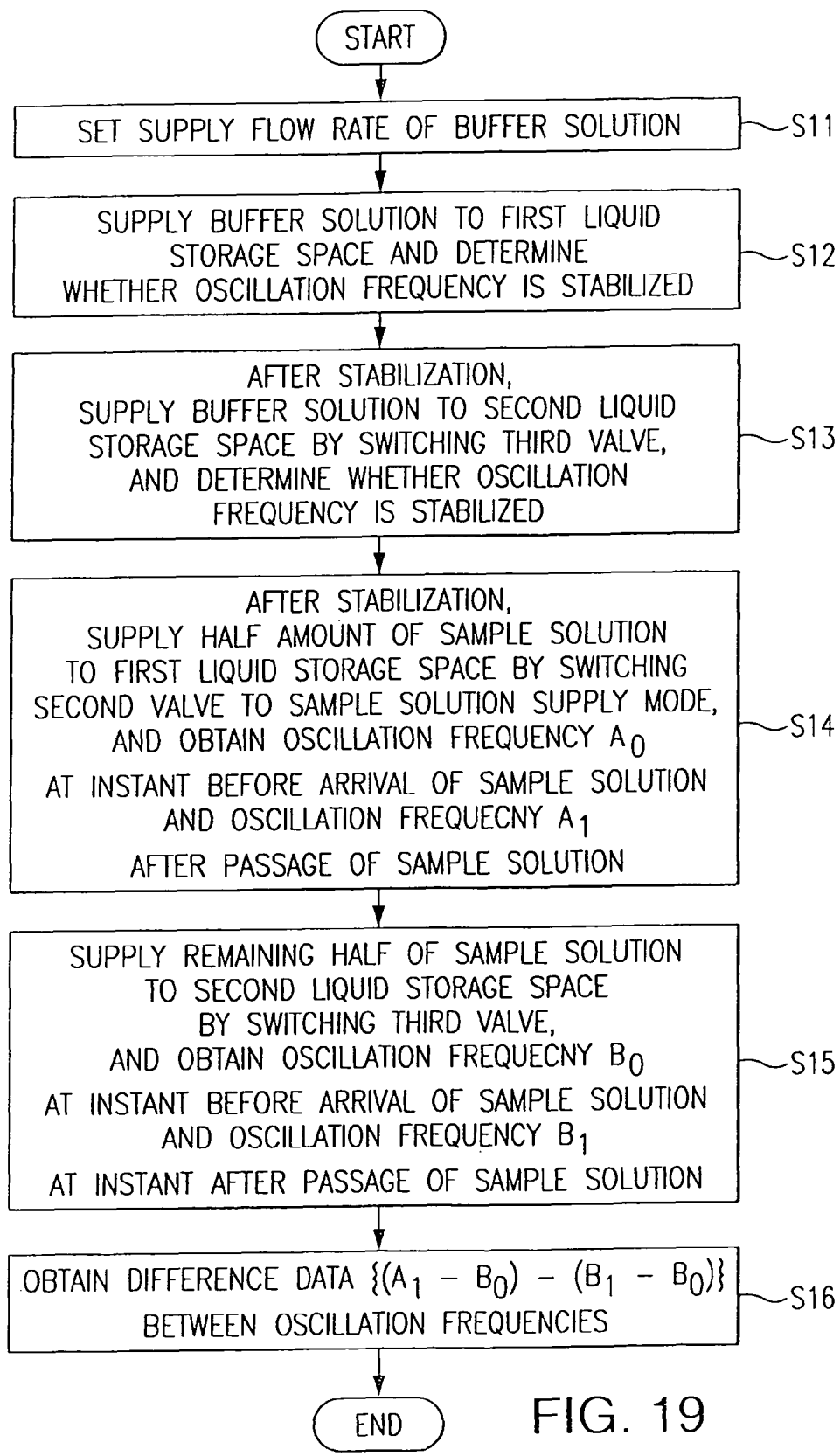
FIG. 19 is an explanatory flowchart showing the operation of the sensing device in the other example.

Then, as shown in FIG. 19, at the time of the measurement, the supply flow rate of the buffer solution is first set, for instance (Step S11) and the sample solution is supplied so as to fill the injection loop 14a. Next, the channel system is set to the state shown in FIG. 14(a) to supply the buffer solution into the first liquid storage space 51A, and it is determined whether or not the oscillation frequency is stabilized (Step S12). When it is determined that the oscillation frequency is stabilized, by switching the third valve 15 to the position for supplying the liquid to the second liquid storage space 51B, the buffer solution is supplied into the second liquid storage space 51B and it is determined whether or not the oscillation frequency is stabilized (Step S13).

Then, when it is determined that the oscillation frequency is stabilized, by switching the second valve 14 to the sample solution supply mode, the sample solution in the injection loop 14a is supplied into the first liquid storage space 51A, and the oscillation frequency A0 at the instant T30 before the sample solution reaches the quartz-crystal resonator 4 (first liquid storage space 51A) and the oscillation frequency A1 at the instant T51 after the sample solution passes through the first liquid storage space 51A are obtained (Step S14). After a half amount of the sample solution in the injection loop 14a is thus supplied to the first liquid storage space 51A, by switching the third valve 15, the remaining sample solution is supplied into the second liquid storage space 51B, and the oscillation frequency B0 at the instant T40 before the sample solution reaches the quartz-crystal resonator 4 (second liquid storage space 51B) and the oscillation frequency B1 at the instant T61 after the sample solution passes through the second liquid storage space 51B are obtained (Step S15). Next, the differences (A1−A0), (B1−B0) of the oscillation frequencies of the oscillator circuits 6A, 6B are obtained, for instance, and the difference data {(A1−A0)−(B1−B0)} therebetween is obtained (Step S16).

In the foregoing, in the present invention, the sample solution is not limited to blood, serum, or the like but may be environmental water of a river or the like. Further, the substance to be sensed may be CRP (C-reactive protein) or the like employed in the measurement such as disease inspection or may be an environmental pollutant. An example of the environmental pollutant is dioxin. Further, when blood or serum is used as the sample solution, the buffer solution is preferably used as the reference liquid. However, the reference liquid is not limited to the buffer solution and may be, for example, pure water, salt water, or the like.

What is claimed is:

1. A sensing device in which a piezoelectric sensor including a piezoelectric resonator is mounted and which senses a substance to be sensed in a sample solution based on an oscillation frequency obtained when the sample solution flows from a supply channel to one surface side of the piezoelectric resonator, the sensing device comprising:

a reference liquid supply part provided to supply a reference liquid to the supply channel and capable of varying a supply flow rate of the reference liquid;

a sample solution storage channel which is interposed between the reference liquid supply part and the supply channel to temporarily store the sample solution, and from which the sample solution is sent to the supply channel by being pushed by the reference liquid supplied from the reference liquid supply part;

a channel switching part switching a channel between a reference liquid supply mode in which the reference liquid supply part is connected to the supply channel not via the sample solution storage channel and a sample solution supply mode in which the reference liquid supply part is connected to the supply channel via the sample solution storage channel;

a control part determining whether or not the oscillation frequency is stabilized while the reference liquid is supplied to the piezoelectric resonator from the reference liquid supply part, and when determining that the oscillation frequency is stabilized, switches the channel switching part to the sample solution supply mode in order to cause the supply of the sample solution in the storage channel to the piezoelectric resonator;

a flow rate setting part via which the supply flow rate of the reference liquid supply part is set; and a computing part which finds an instant at which the sample solution reaches the piezoelectric resonator and an instant at which the sample solution finishes passing through the piezoelectric resonator, based on the supply flow rate of the reference liquid set via the flow rate setting part, a volume of the sample solution storage channel, a volume of the supply channel, and an instant at which the channel switching part is switched to the sample solution supply mode, and finds an oscillation frequency during a period from the switching instant to an instant before the sample solution reaches the piezoelectric resonator and an oscillation frequency after the sample solution passes through the piezoelectric resonator to obtain a difference between the oscillation frequencies.

2. The sensing device according to claim 1, wherein a liquid feed pump is used as the reference liquid supply part, the sensing device further comprising:

a cleaning liquid supply part interposed between the sample solution storage channel and the supply channel to supply a cleaning liquid to the storage channel; and a downstream-side channel switching part provided on a downstream side of the channel switching part to switch a channel between a liquid supply mode in which the storage channel and the supply channel are connected and a cleaning mode in which the storage channel and the cleaning liquid supply part are connected, and wherein for cleaning the storage channel, the channel switching part is switched to the sample solution supply mode, the downstream-side channel switching part is switched to the cleaning mode, and the cleaning liquid is sucked into the storage channel from the cleaning liquid supply part by the reference liquid supply part.

* * * * *